US012642657B2

(12) United States Patent
Reed

(10) Patent No.: US 12,642,657 B2
(45) Date of Patent: Jun. 2, 2026

---

(54) CATHETERS FOR IMPLANTS AND MEDICAL PROCEDURES AND METHODS OF USE THEREOF

(71) Applicant: EDWARDS LIFESCIENCES CORPORATION, Irvine, CA (US)

(72) Inventor: Kurt Kelly Reed, Huntington Beach, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 623 days.

(21) Appl. No.: 18/312,553

(22) Filed: May 4, 2023

(65) Prior Publication Data

US 2023/0270551 A1     Aug. 31, 2023

Related U.S. Application Data

(63) Continuation of application No. PCT/US2021/057930, filed on Nov. 3, 2021.

(60) Provisional application No. 63/109,461, filed on Nov. 4, 2020.

(51) Int. Cl.
*A61F 2/24*          (2006.01)

(52) U.S. Cl.
CPC .......... *A61F 2/2466* (2013.01); *A61F 2/2445* (2013.01); *A61F 2230/0091* (2013.01)

(58) Field of Classification Search
CPC .................. A61F 2/2466; A61F 2/2445; A61F 2230/0091; A61F 2002/9623; A61F 2/2436; A61F 2/2409; A61F 2/2418
See application file for complete search history.

(56) References Cited

U.S. PATENT DOCUMENTS

| | | | |
|---|---|---|---|
| 519,297 | A | 5/1894 | Bauer |
| 4,035,849 | A | 7/1977 | Angell et al. |
| 4,592,340 | A | 6/1986 | Boyles |
| 4,955,895 | A | 9/1990 | Sugiyama et al. |
| 4,994,077 | A | 2/1991 | Dobben |
| 5,059,177 | A | 10/1991 | Towne et al. |
| 5,176,698 | A | 1/1993 | Burns et al. |
| 5,192,297 | A | 3/1993 | Hull |
| 5,266,073 | A | 11/1993 | Wall |
| 5,325,845 | A | 7/1994 | Adair |
| 5,358,496 | A | 10/1994 | Ortiz et al. |
| 5,411,552 | A | 5/1995 | Andersen et al. |
| 5,554,185 | A | 9/1996 | Block et al. |
| 5,591,195 | A | 1/1997 | Taheri et al. |
| 5,599,305 | A | 2/1997 | Hermann et al. |
| 5,632,760 | A | 5/1997 | Sheiban et al. |
| 5,639,274 | A | 6/1997 | Fischell et al. |

(Continued)

FOREIGN PATENT DOCUMENTS

| | | |
|---|---|---|
| DE | 19532846 A1 | 3/1997 |
| DE | 19907646 A1 | 8/2000 |

(Continued)

*Primary Examiner* — Yashita Sharma
*Assistant Examiner* — Jose H. Trevino, III
(74) *Attorney, Agent, or Firm* — Snell and Wilmer LLP

(57)          ABSTRACT

A delivery catheter is in various embodiments configured to deliver an anchoring device to a native valve annulus of a patient's heart, where the anchoring device can better secure a prosthesis at the native annulus. The delivery catheter may include a flexible portion configured to form a spiral shape in embodiments.

20 Claims, 35 Drawing Sheets

(56) References Cited

U.S. PATENT DOCUMENTS

| | | | |
|---|---|---|---|
| 5,728,068 A | 3/1998 | Leone et al. |
| 5,749,890 A | 5/1998 | Shaknovich |
| 5,782,809 A | 7/1998 | Umeno et al. |
| 5,824,044 A | 10/1998 | Quiachon et al. |
| 5,840,081 A | 11/1998 | Andersen et al. |
| 5,908,405 A | 6/1999 | Imran et al. |
| 5,916,147 A | 6/1999 | Boury |
| 5,944,690 A | 8/1999 | Falwell et al. |
| 5,961,536 A | 10/1999 | Mickley et al. |
| 5,968,068 A | 10/1999 | Dehdashtian et al. |
| 6,019,777 A | 2/2000 | Mackenzie |
| 6,027,510 A | 2/2000 | Alt |
| 6,033,381 A | 3/2000 | Kontos |
| 6,143,016 A | 11/2000 | Bleam et al. |
| 6,162,208 A | 12/2000 | Hipps |
| 6,168,614 B1 | 1/2001 | Andersen et al. |
| 6,174,327 B1 | 1/2001 | Mertens et al. |
| 6,217,585 B1 | 4/2001 | Houser et al. |
| 6,235,050 B1 | 5/2001 | Quiachon et al. |
| 6,251,092 B1 | 6/2001 | Qin et al. |
| 6,379,372 B1 | 4/2002 | Dehdashtian et al. |
| 6,383,171 B1 | 5/2002 | Gifford et al. |
| 6,454,799 B1 | 9/2002 | Schreck |
| 6,458,153 B1 | 10/2002 | Bailey et al. |
| 6,461,382 B1 | 10/2002 | Cao |
| 6,471,672 B1 | 10/2002 | Brown et al. |
| 6,500,147 B2 | 12/2002 | Omaleki et al. |
| 6,514,228 B1 | 2/2003 | Hamilton et al. |
| 6,527,979 B2 | 3/2003 | Constantz et al. |
| 6,579,305 B1 | 6/2003 | Lashinski |
| 6,582,462 B1 | 6/2003 | Andersen et al. |
| 6,652,578 B2 | 11/2003 | Balley et al. |
| 6,730,118 B2 | 5/2004 | Spenser et al. |
| 6,733,525 B2 | 5/2004 | Yang et al. |
| 6,764,504 B2 | 7/2004 | Wang et al. |
| 6,767,362 B2 | 7/2004 | Schreck |
| 6,830,584 B1 | 12/2004 | Seguin |
| 6,893,460 B2 | 5/2005 | Spenser et al. |
| 6,908,481 B2 | 6/2005 | Cribier |
| 7,011,094 B2 | 3/2006 | Rapacki et al. |
| 7,018,406 B2 | 3/2006 | Seguin et al. |
| 7,018,408 B2 | 3/2006 | Bailey et al. |
| 7,137,993 B2 | 11/2006 | Acosta et al. |
| 7,276,084 B2 | 10/2007 | Yang et al. |
| 7,318,278 B2 | 1/2008 | Zhang et al. |
| 7,320,702 B2 | 1/2008 | Hammersmark et al. |
| 7,320,704 B2 | 1/2008 | Lashinski et al. |
| 7,374,571 B2 | 5/2008 | Pease et al. |
| 7,393,360 B2 | 7/2008 | Spenser et al. |
| 7,435,257 B2 | 10/2008 | Lashinski et al. |
| 7,510,575 B2 | 3/2009 | Spenser et al. |
| 7,585,321 B2 | 9/2009 | Cribier |
| 7,594,926 B2 | 9/2009 | Linder et al. |
| 7,597,709 B2 | 10/2009 | Goodin |
| 7,618,446 B2 | 11/2009 | Andersen et al. |
| 7,780,723 B2 | 8/2010 | Taylor |
| 7,785,366 B2 | 8/2010 | Maurer et al. |
| 7,959,661 B2 | 6/2011 | Hijlkema et al. |
| 8,029,556 B2 | 10/2011 | Rowe |
| 8,167,932 B2 | 5/2012 | Bourang et al. |
| RE43,882 E | 12/2012 | Hopkins et al. |
| 8,449,606 B2 | 5/2013 | Ellasen et al. |
| 8,475,523 B2 | 7/2013 | Duffy |
| 8,568,472 B2 | 10/2013 | Marchand et al. |
| 9,061,119 B2 | 6/2015 | Le et al. |
| 9,119,716 B2 | 9/2015 | Lee et al. |
| 9,795,477 B2 | 10/2017 | Tran et al. |
| 11,273,038 B2 | 3/2022 | Tang et al. |
| 2001/0002445 A1 | 5/2001 | Vesely |
| 2001/0007082 A1 | 7/2001 | Dusbabek et al. |
| 2002/0032481 A1 | 3/2002 | Gabbay |
| 2002/0058995 A1 | 5/2002 | Stevens |
| 2002/0165461 A1 | 11/2002 | Hayzelden et al. |
| 2003/0040792 A1 | 2/2003 | Gabbay |
| 2003/0050694 A1 | 3/2003 | Yang et al. |
| 2003/0120341 A1 | 6/2003 | Shennib et al. |
| 2004/0093061 A1 | 5/2004 | Acosta et al. |
| 2004/0133263 A1 | 7/2004 | Dusbabek et al. |
| 2004/0143197 A1 | 7/2004 | Soukup et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0080474 A1 | 4/2005 | Andreas et al. |
| 2005/0096736 A1 | 5/2005 | Osse et al. |
| 2005/0137689 A1 | 6/2005 | Salahieh et al. |
| 2005/0149160 A1 | 7/2005 | McFerran |
| 2005/0203614 A1 | 9/2005 | Forster et al. |
| 2005/0203617 A1 | 9/2005 | Forster et al. |
| 2005/0245894 A1 | 11/2005 | Zadno-Azizi |
| 2006/0025857 A1 | 2/2006 | Bergheim et al. |
| 2006/0282150 A1 | 12/2006 | Olson et al. |
| 2007/0005131 A1 | 1/2007 | Taylor |
| 2007/0073389 A1 | 3/2007 | Bolduc et al. |
| 2007/0088431 A1 | 4/2007 | Bourang et al. |
| 2007/0100356 A1 | 5/2007 | Lucatero et al. |
| 2007/0112422 A1 | 5/2007 | Dehdashtian |
| 2007/0203575 A1 | 8/2007 | Forster et al. |
| 2007/0219612 A1 | 9/2007 | Andreas et al. |
| 2007/0239254 A1 | 10/2007 | Chia et al. |
| 2007/0244546 A1 | 10/2007 | Francis |
| 2007/0265700 A1 | 11/2007 | Eliasen et al. |
| 2008/0065011 A1 | 3/2008 | Marchand et al. |
| 2008/0103520 A1 | 5/2008 | Selkee |
| 2008/0125853 A1 | 5/2008 | Bailey et al. |
| 2008/0294230 A1 | 11/2008 | Parker |
| 2009/0024428 A1 | 1/2009 | Hudock, Jr. |
| 2009/0069889 A1 | 3/2009 | Suri et al. |
| 2009/0138079 A1 | 5/2009 | Tuval et al. |
| 2009/0157175 A1 | 6/2009 | Benichou |
| 2009/0192585 A1 | 7/2009 | Bloom et al. |
| 2009/0228093 A1 | 9/2009 | Taylor et al. |
| 2009/0276040 A1 | 11/2009 | Rowe et al. |
| 2009/0281619 A1 | 11/2009 | Le et al. |
| 2009/0299456 A1 | 12/2009 | Melsheimer |
| 2009/0319037 A1 | 12/2009 | Rowe et al. |
| 2010/0030318 A1 | 2/2010 | Berra |
| 2010/0036472 A1 | 2/2010 | Papp |
| 2010/0036473 A1 | 2/2010 | Roth |
| 2010/0049313 A1 | 2/2010 | Alon et al. |
| 2010/0076402 A1 | 3/2010 | Mazzone et al. |
| 2010/0076541 A1 | 3/2010 | Kumoyama |
| 2010/0082089 A1 | 4/2010 | Quadri et al. |
| 2010/0094394 A1 | 4/2010 | Beach et al. |
| 2010/0121425 A1 | 5/2010 | Shimada |
| 2010/0145431 A1 | 6/2010 | Wu et al. |
| 2010/0161036 A1 | 6/2010 | Pintor et al. |
| 2010/0174363 A1 | 7/2010 | Castro |
| 2010/0198347 A1 | 8/2010 | Zakay et al. |
| 2010/0274344 A1 | 10/2010 | Dusbabek et al. |
| 2011/0015729 A1 | 1/2011 | Jimenez et al. |
| 2011/0054596 A1 | 3/2011 | Taylor |
| 2011/0137331 A1 | 6/2011 | Walsh et al. |
| 2011/0160846 A1 | 6/2011 | Bishop et al. |
| 2012/0123327 A1* | 5/2012 | Miller .............. A61M 25/0136 604/95.04 |
| 2012/0123529 A1 | 5/2012 | Levi et al. |
| 2012/0239142 A1 | 9/2012 | Liu et al. |
| 2013/0030519 A1 | 1/2013 | Tran et al. |
| 2013/0317598 A1 | 11/2013 | Rowe et al. |
| 2014/0296962 A1 | 10/2014 | Cartledge et al. |
| 2017/0065415 A1 | 3/2017 | Rupp et al. |
| 2018/0153689 A1 | 6/2018 | Maimon et al. |
| 2018/0344456 A1 | 12/2018 | Barash et al. |

FOREIGN PATENT DOCUMENTS

| | | | |
|---|---|---|---|
| EP | 0592410 B1 | 10/1995 |
| EP | 0850607 A1 | 7/1998 |
| FR | 2815844 A1 | 5/2002 |
| WO | 9117720 A1 | 11/1991 |
| WO | 9829057 A1 | 7/1998 |
| WO | 9912483 A1 | 3/1999 |
| WO | 0149213 A2 | 7/2001 |
| WO | 0154625 A1 | 8/2001 |

(56) References Cited

FOREIGN PATENT DOCUMENTS

| | | | |
|---|---|---|---|
| WO | 0176510 | A2 | 10/2001 |
| WO | 0222054 | | 3/2002 |
| WO | 0236048 | A1 | 5/2002 |
| WO | 0247575 | A2 | 6/2002 |
| WO | 02060352 | | 8/2002 |
| WO | 03030776 | A2 | 4/2003 |
| WO | 03047468 | | 6/2003 |
| WO | 2004019825 | A1 | 3/2004 |
| WO | 2005084595 | A1 | 9/2005 |
| WO | 2005102015 | A2 | 11/2005 |
| WO | 2006032051 | A2 | 3/2006 |
| WO | 2006111391 | A1 | 10/2006 |
| WO | 2006138173 | A2 | 12/2006 |
| WO | 2007047488 | A2 | 4/2007 |
| WO | 2007067942 | A1 | 6/2007 |
| WO | 2010121076 | A2 | 10/2010 |

* cited by examiner

58

51

56

50

63

52

59

61

62

A1P1

54

62

50

53

A3P3

CATHETERS FOR IMPLANTS AND MEDICAL PROCEDURES AND METHODS OF USE THEREOF

CROSS-REFERENCE TO RELATED APPLICATIONS

This application is a continuation of PCT patent application no. PCT/US2021/057930, filed Nov. 3, 2021, which claims the benefit of U.S. Provisional Application No. 63/109,461, filed Nov. 4, 2020, the entire contents of each of which is incorporated herein by this specific reference.

BACKGROUND

Field

The present disclosure generally concerns deployment tools for delivering anchoring devices, such as prosthetic docking devices that support prostheses and methods of using the same. For example, the disclosure relates to replacement of heart valves that have malformations and/or dysfunctions, where a flexible delivery catheter is utilized to deploy anchoring devices that support a prosthetic heart valve at an implant site, and methods of using the delivery catheter to implant such anchoring devices and/or prosthetic heart valves.

BACKGROUND

Referring generally to FIGS. 1A-1B, the native mitral valve 50 controls the flow of blood from the left atrium 51 to the left ventricle 52 of the human heart and, similarly, the tricuspid valve 59 controls the flow of blood between the right atrium 56 and the right ventricle 61. The mitral valve has a different anatomy than other native heart valves. The mitral valve includes an annulus made up of native valve tissue surrounding the mitral valve orifice, and a pair of cusps or leaflets extending downward from the annulus into the left ventricle. The mitral valve annulus can form a "D" shaped, oval shaped, or otherwise non-circular cross-sectional shape having major and minor axes. An anterior leaflet can be larger than a posterior leaflet of the valve, forming a generally "C" shaped boundary between the abutting free edges of the leaflets when they are closed together.

When operating properly, the anterior leaflet 54 and the posterior leaflet 53 of the mitral valve function together as a one-way valve to allow blood to flow from the left atrium 51 to the left ventricle 52. After the left atrium receives oxygenated blood from the pulmonary veins, the muscles of the left atrium contract and the left ventricle relaxes (also referred to as "ventricular diastole" or "diastole"), and the oxygenated blood that is collected in the left atrium flows into the left ventricle. Then, the muscles of the left atrium relax and the muscles of the left ventricle contract (also referred to as "ventricular systole" or "systole"), to move the oxygenated blood out of the left ventricle 52 and through the aortic valve 63 and the aorta 58 to the rest of the body. The increased blood pressure in the left ventricle during ventricular systole urges the two leaflets of the mitral valve together, thereby closing the one-way mitral valve so that blood cannot flow back into the left atrium. To prevent or inhibit the two leaflets from prolapsing under the pressure and folding back through the mitral annulus toward the left atrium during ventricular systole, a plurality of fibrous cords 62 called chordae tendineae tether the leaflets to papillary muscles in the left ventricle. The chordae tendineae 62 are schematically illustrated in both the heart cross-section of FIG. 1A and the top view of the mitral valve in FIG. 1B.

Problems with the proper functioning of the mitral valve are a type of valvular heart disease. Vascular heart disease can affect the other heart valves as well, including the tricuspid valve. A common form of valvular heart disease is valve leak, also known as regurgitation, which can occur in various heart valve, including both the mitral and tricuspid valves. Mitral regurgitation occurs when the native mitral valve fails to close properly and blood flows back into the left atrium from the left ventricle during ventricular systole. Mitral regurgitation can have different causes, such as leaflet prolapse, dysfunctional papillary muscles, problems with chordae tendineae, and/or stretching of the mitral valve annulus resulting from dilation of the left ventricle. In addition to mitral regurgitation, mitral narrowing or stenosis is another example of valvular heart disease. In tricuspid regurgitation, the tricuspid valve fails to close properly and blood flows back into the right atrium from the right ventricle.

Like the mitral and tricuspid valves, the aortic valve is likewise susceptible to complications, such as aortic valve stenosis or aortic valve insufficiency. One method for treating aortic heart disease includes the use of a prosthetic valve implanted within the native aortic valve. These prosthetic valves can be implanted using a variety of techniques, including various transcatheter techniques. A transcatheter heart valve (THV) can be mounted in a crimped state on the end portion of a flexible and/or steerable catheter, advanced to the implantation site in the heart via a blood vessel connected to the heart, and then expanded to its functional size, for example, by inflating a balloon on which the THV is mounted. Alternatively, a self-expanding THV can be retained in a radially compressed state within a sheath of a delivery catheter, where the THV can be deployed from the sheath, which allows the THV to expand to its functional state. Such delivery catheters and techniques of implantation are generally more developed for implantation or use at the aortic valve, but do not address the unique anatomy and challenges of other valves.

SUMMARY

This summary is meant to provide some examples and is not intended to be limiting of the scope of the invention in any way. For example, any feature included in an example of this summary is not required by the claims, unless the claims explicitly recite the features. Also, the features described can be combined in a variety of ways. Various features and steps as described elsewhere in this disclosure may be included in the examples summarized here.

Tools and methods are provided for mitral and tricuspid valve replacements, including for adapting different types of implants such as valve or valves (e.g., those designed for aortic valve replacement or other locations) for use at the mitral and tricuspid valve locations. One way of adapting these other prosthetic valves at the mitral position or tricuspid position is to deploy the prosthetic valves into an implant such as an anchor or other docking device/station that will form a more appropriately shaped implant site at the native valve annulus. The anchor or other docking device/stations herein allow a prosthetic valve to be implanted more securely, while also reducing or eliminating leakage around the valve after implantation.

One type of implant in the form of an anchor or anchoring device that can be used herein is a docking coil including a coil or helically shaped anchor that provides for a circular or cylindrical docking site for cylindrically shaped prosthetic valves. One type of anchor or anchoring device that can be used herein includes a coiled region and/or helically shaped region that provides for a circular or cylindrical docking site for cylindrically shaped prosthetic valves. In this manner, optionally an existing valve implant developed for the aortic position, perhaps with some modification, can be implanted at another valve position such as the mitral position together with such an anchor or anchoring device. Such anchors or anchoring devices can be used at the heart's other native valves, such as the tricuspid valve, to more securely anchor prosthetic valves at those sites as well.

Described herein are embodiments of deployment tools to assist in delivering implants in the form of prosthetic devices at one of the native mitral, aortic, tricuspid, or pulmonary valve regions of a human heart, as well as methods for using the same. The disclosed deployment tools can be used to deploy implants in the form of anchoring devices (e.g., prostheses docking devices, prosthetic valve docking devices, etc.), such as helical anchoring devices or anchoring devices having a plurality of turns or coils, at the implantation site to provide a foundational support structure into which a prosthetic heart valve can be implanted. A delivery catheter may comprise a steerable delivery catheter in embodiments.

In one embodiment, a delivery catheter may include an elongate shaft having a flexible portion, and a spine including an elongate strip extending longitudinally in a spiral along a first portion of the flexible portion. A tether may extend longitudinally in a spiral along a second portion of the flexible portion that is circumferentially spaced from the first portion. The flexible portion may be configured to form a spiral shape upon a longitudinal force being applied to the tether.

A method may include delivering a delivery catheter to a portion of a patient's body, the delivery catheter including an elongate shaft having a flexible portion, and a spine including an elongate strip extending longitudinally in a spiral along a first portion of the flexible portion. A tether may extend longitudinally in a spiral along a second portion of the flexible portion that is circumferentially spaced from the first portion.

The method may include applying a longitudinal force to the tether to form the flexible portion into a spiral shape.

The systems and catheters summarized here can also include any of the features, components, elements, etc. described elsewhere in this disclosure, and the methods summarized here can also include any of the steps described elsewhere in this disclosure.

BRIEF DESCRIPTION OF THE DRAWINGS

The foregoing and other objects, features, and advantages of the disclosure will become more apparent from the following detailed description using the accompanying figures. In the drawings:

FIG. 8I illustrates the anchoring device of FIG. 8G further wrapping around the chordae tendineae and leaflets in the left ventricle of the patient's heart as it is being delivered by the delivery catheter of FIG. 8A;

FIG. 8O is a cutout view of the patient's heart that illustrates an exemplary embodiment of a prosthetic heart valve being delivered by an exemplary embodiment of a heart valve delivery device to the mitral valve of the patient;

DETAILED DESCRIPTION

The following description and accompanying figures, which describe and show certain embodiments, are made to demonstrate, in a non-limiting manner, several possible configurations of systems, devices, apparatuses, components, methods, etc. that may be used for various aspects and features of the present disclosure. As one example, various systems, devices/apparatuses, components, methods, etc. are described herein that may relate to mitral valve procedures. However, specific examples provided are not intended to be limiting, e.g., the systems, devices/apparatuses, components, methods, etc. can be adapted for use in other valves beyond the mitral valve (e.g., in the tricuspid valve).

Described herein are embodiments of deployment tools that are intended to facilitate implantation of implants in the form of prosthetic devices (e.g., prosthetic valves) at one of the native mitral, aortic, tricuspid, or pulmonary valve regions of a human heart, as well as methods for using the same. The prosthetic devices or valves can be expandable transcatheter heart valves ("THVs") (e.g., balloon expandable, self-expandable, and/or mechanically expandable THVs). The deployment tools can be used to deploy anchoring devices (sometimes referred to as docking devices, docking stations, or similar terms) that provide a more stable docking site to secure the prosthetic device or valve (e.g., THVs) at the native valve region. The anchoring devices may comprise docking coils in embodiments. These deployment tools can be used to more accurately place such anchoring devices (e.g., prostheses anchoring devices, prosthetic valve anchoring device, etc.), so that the anchoring devices and any prostheses (e.g., prosthetic devices or prosthetic heart valves) anchored thereto function properly after implantation.

Figures 1A, 1B:
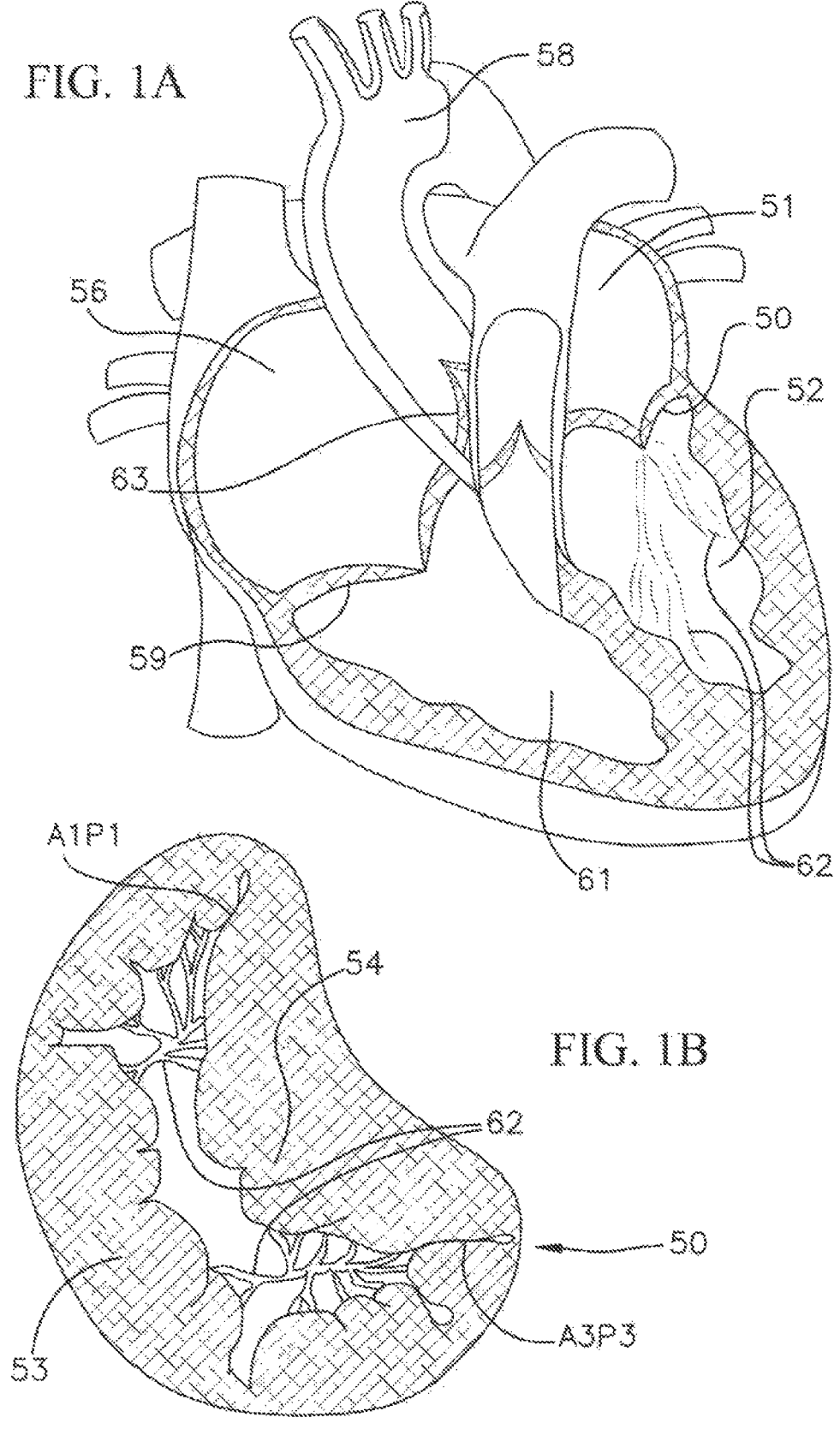
FIG. 1A shows a schematic cross-sectional view of a human heart.
FIG. 1B shows a schematic top view of the mitral valve annulus of a heart.
Figure 2A:
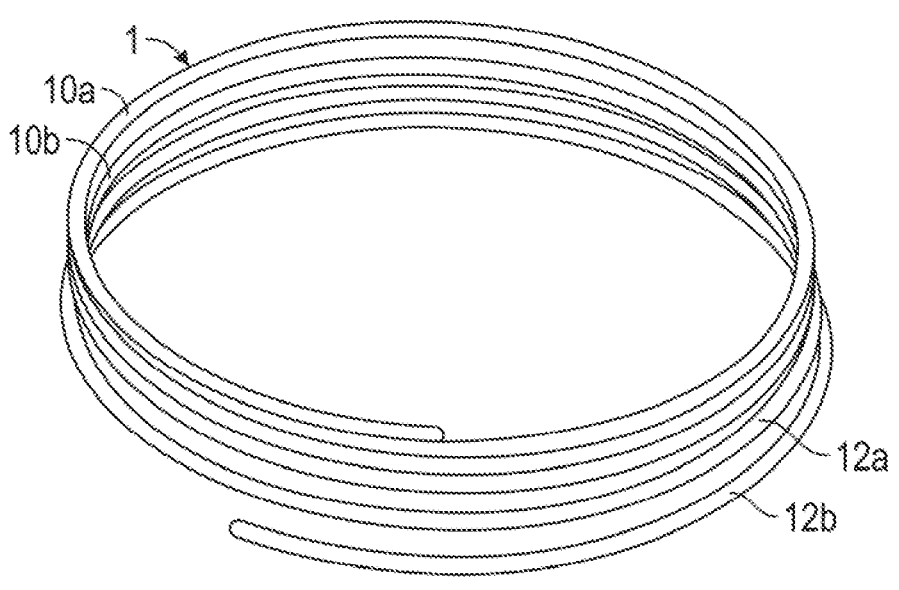
FIG. 2A shows a perspective view of an exemplary anchoring device that is helical.

An example of one such implant includes an anchoring device comprising a docking coil as shown in FIG. 2A. Other examples of anchoring devices that can be used herein are shown in U.S. patent application Ser. Nos. 15/643,229, 15/684,836, and 15/682,287, which are each incorporated by reference in their entirety herein. The anchoring devices herein can be coiled or helical or they can include one or more coiled or helical regions. Anchoring device 1 is shown in FIG. 2A as including two upper coils 10_a_, 10_b_ and two lower coils 12_a_, 12_b_. In alternative embodiments, the anchoring device 1 can include any suitable number of upper coils and lower coils. For example, the anchoring device 1 can include one upper coil, two or more upper coils, three or more upper coils, four or more upper coils, five or more upper coils, etc. In addition, the anchoring device 1 can have one lower coil, two or more lower coils, three or more lower coils, four or more lower coils, five or more lower coils, etc. In various embodiments, the anchoring device 1 can have the same number of upper coils as it has lower coils. In other embodiments, the anchoring device 1 can have more or less upper coils as compared to lower coils.

Implants in the form of anchoring devices can include coils/turns of varying diameters or the same diameters, coils/turns spaced with varying gap sizes or no gaps, and coils/turns which taper, expand, or flare to become larger or smaller. It should be noted that the coils/turns can also stretch radially outward when a prosthetic valve is placed or expanded within anchoring device 1.

In the illustrated embodiment of FIG. 2A, the upper coils 10a, 10b can be about the same size as or can have a slightly smaller diameter than the lower coils 12a, 12b. One or more lower end coils/turns (e.g., a full or partial end coil/turn) can have a larger diameter or larger radius of curvature than other coils and act as an encircling coil/turn to help guide the end of the coil outside and around the leaflets and/or any chordae tendineae, e.g., to encircle and corral the leaflets and/or any chordae tendineae. One or more larger-diameter or larger-radius lower coils or encircling coils allow for easier engagement with the native valve annulus and navigation around the native valve anatomy during insertion.

In some embodiments, one or more upper coils/turns (e.g., full or partial coils/turns) can be larger or have a larger diameter (or radius of curvature) and act as a stabilization coil (e.g., in an atrium of the heart) to help hold the coil in position before the prosthetic valve is deployed therein. In some embodiments, the one or more upper coils/turns can be atrial coils/turns and can have a greater diameter than the coils in the ventricle, for example, acting as a stabilization coil/turn configured to engage an atrial wall for stability.

Some of the coils can be functional coils (e.g., coils/turns between the stabilization coil(s)/turn(s) and the encircling coil(s)/turn(s)) in which the prosthetic valve is deployed and forces between the functional coils and prosthetic valve help to hold each other in position. The anchoring device and prosthetic valve may pinch native tissue (e.g., leaflets and/or chordae) between themselves (e.g., between the functional coils of the anchoring device and an outer surface of the prosthetic valve) to more securely hold them in place.

In one embodiment, which can be the same as or similar to the anchoring device shown in FIGS. 8G-8S, an anchoring device may have one large upper coil/turn or stabilization coil/turn, one lower end coil/turn or encircling coil/turn, and multiple functional coils/turn (e.g., 2, 3, 4, 5, or more functional coils/turns).

Figure 2B:
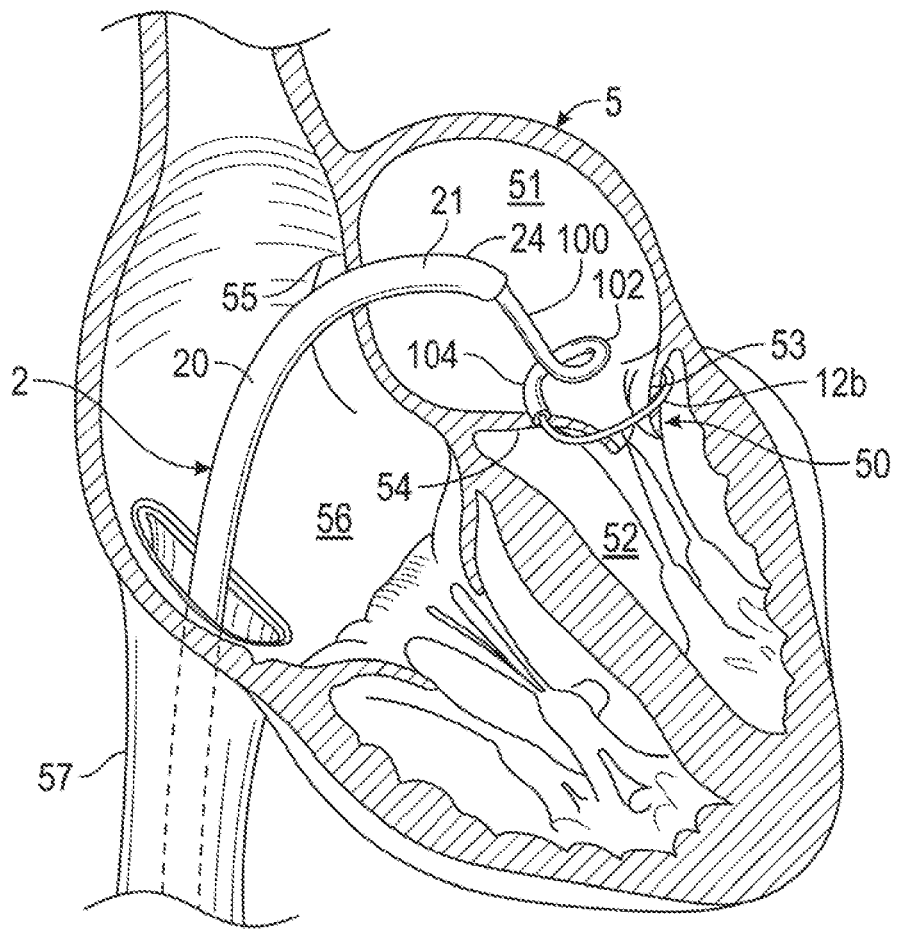
FIG. 2B shows a partial perspective view of an exemplary delivery catheter for implanting an implant in the form of an anchoring device at a native valve of a heart, using a transseptal technique.
Figure 2C:
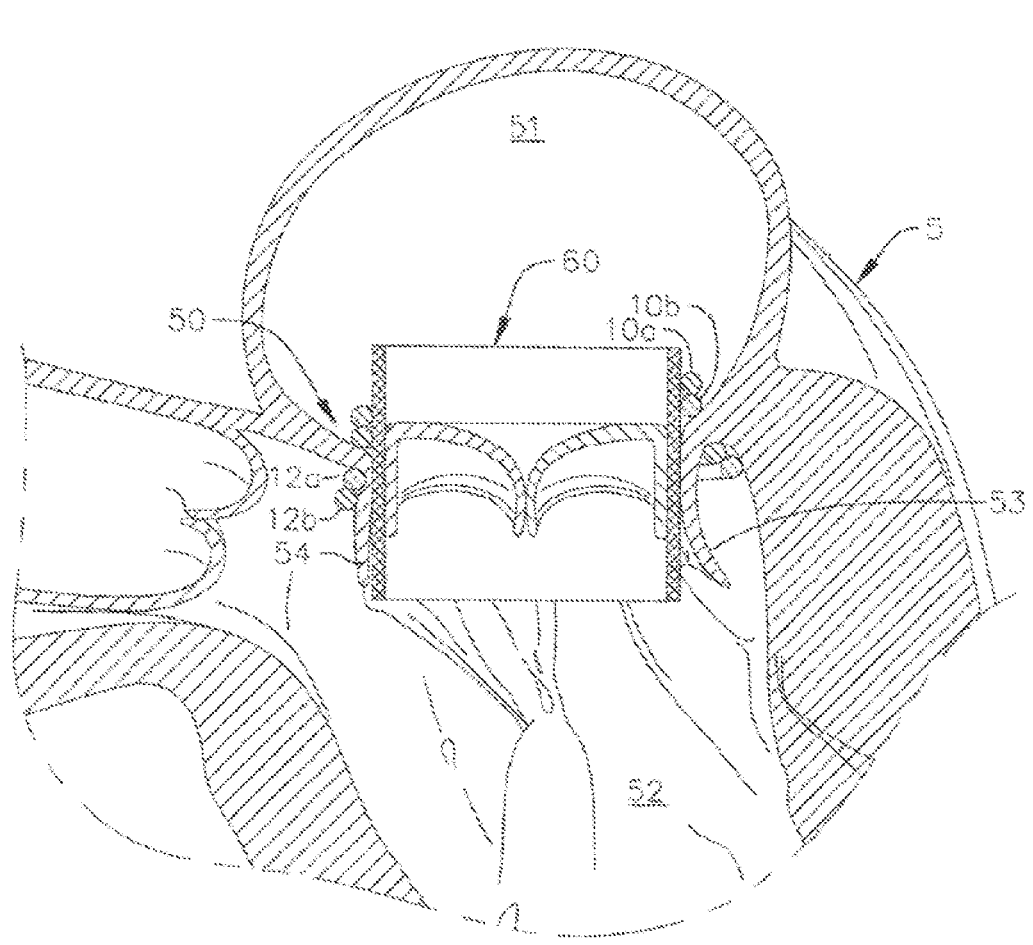
FIG. 2C shows a cross-sectional view of an anchoring device and an exemplary prosthetic heart valve implanted at the native valve of the heart.

When used at the mitral position, the anchoring device can be implanted so that one or more upper coils/turns (e.g., the upper coils 10a, 10b) are above, i.e., on the atrial side, of the annulus of the native valve (e.g., mitral valve 50 or a tricuspid valve) and the lower coils 12a, 12b are below, i.e., on the ventricular side, of the annulus of the native valve, for example, as shown in FIG. 2C. In this configuration, the mitral leaflets 53, 54 can be captured between the upper coils 10a, 10b and the lower coils 12a, 12b. When implanted, the various anchoring devices herein can provide a solid support structure to secure a prosthetic valve in place and avoid migration due to the operation of the heart.

FIG. 2B shows a delivery device 2 for installing an implant in the form of an anchoring device at a native mitral valve annulus 50 using a transseptal technique. The same or a similar delivery device 2 could be used to deliver an anchoring device at the tricuspid valve without having to leave the right atrium to cross the septum into the left atrium. The delivery device 2 includes a sheath catheter including an outer sheath or guide sheath 20. The delivery device includes a delivery catheter 100. The sheath 20 has a shaft in the shape of an elongated hollow tube through which the delivery catheter 100, as well as various other components (e.g., implants such as the anchoring device and a prosthetic heart valve, etc.), can pass, thus allowing the components to be introduced into the patient's heart 5. The sheath 20 can be steerable so that the sheath 20 can be bent at various angles needed for the sheath to pass through the heart 5 and enter the left atrium 51. The sheath 20 may comprise a steerable guide sheath including a lumen for a delivery catheter to pass through. The steerable guide sheath may be configured to deflect a portion of an elongate shaft of the delivery catheter 100 when the elongate shaft is positioned within the lumen of the steerable guide sheath. While in the sheath 20, the delivery catheter 100 has a relatively straight or straightened shape (compared to a spiral shape discussed in greater detail below), e.g., the delivery catheter 100 is held in sheath 20 in a configuration or shape that corresponds to the configuration or shape of the sheath 20.

Like the sheath 20, the delivery catheter 100 has an elongate shaft having the shape of an elongated hollow tube. However, the delivery catheter 100 has a smaller diameter than the sheath 20 so that it can slide axially within the sheath 20. Meanwhile, the delivery catheter 100 is large enough to house and deploy an implant such as an anchoring device, such as the anchoring device 1.

The elongate shaft of the delivery catheter 100 may have a flexible portion 102. The flexible portion 102 may comprise a distal portion of the elongate shaft of the delivery catheter 100. The flexible portion 102 may be configured to form a spiral shape. The flexible portion 102 may be configured to bend or otherwise move from a straightened shape to a spiral shape. The flexible portion 102 may bend into a configuration that allows for more accurate placement of the anchoring device 1, and in general should have a robust design that allows for the flexible portion 102 to be bent and held at such configuration. For example, as shown in FIG. 2B, the flexible portion 102 may bend into a spiral shape in which a distal portion 104 of the flexible portion 102 is curved to assist in extrusion or pushing out of the anchoring device 1 on a ventricular side of the mitral valve 50, so that the lower coils (e.g., functional coils and/or encircling coils) of the anchoring device 1 can be properly installed below the annulus of the native valve. The flexible portion 102 can also be bent into the spiral shape so that the upper coil(s) (e.g., a stabilization coil/turn or upper coils 10a, 10b) of the anchoring device can be accurately deployed on the atrial side of the annulus of the native valve. For example, the flexible portion 102 can have a spiral shape for installing the upper coils 10a, 10b and a spiral shape for installing the lower coils 12a, 12b. In other embodiments, the flexible portion 102 may have one configuration for installing the lower coils 12a, 12b and another configuration for installing the upper coils 10a, 10b.

In use, when using a transseptal delivery method to access the mitral valve, the sheath 20 can be inserted through a femoral vein, through the inferior vena cava 57 and into the right atrium 56. Alternatively, the sheath 20 can be inserted through a jugular vein or subclavian vein or other upper vasculature location and passed through the superior vena cava and into the right atrium. The interatrial septum 55 is then punctured (e.g., at the fossa ovalis) and the sheath 20 is passed into the left atrium 51, as can be seen in FIG. 2B. (In tricuspid valve procedures, it is unnecessary to puncture or cross the septum 55.) The sheath 20 has a distal end portion 21, which can be a steerable or pre-curved distal end portion to facilitate steering of the sheath 20 into the desired chamber of the heart (e.g., the left atrium 51).

In mitral valve procedures, with the sheath 20 in position in the left atrium 51, the delivery catheter 100 is advanced from the distal end 24 of the sheath 20, such that the flexible portion 102 of the delivery catheter 100 is also in the left atrium 51. In this position, the flexible portion 102 of the delivery catheter 100 can be moved into a spiral shape to allow for an anchoring device 1 to be installed at the annulus of the mitral valve 50. The anchoring device 1 can then be advanced through the delivery catheter 100 and installed at the mitral valve 50. The anchoring device 1 can be attached to a pusher that advances or pushes the anchoring device 1 through the delivery catheter 100 for implantation. The pusher can be a wire or tube with sufficient strength and physical characteristics to push the anchoring device 1 through the delivery catheter 100. In some embodiments, the pusher can be made of or include a spring or coil, a tube extrusion, a braided tube, or a laser cut hypotube, among other structures. In some embodiments, the pusher can have a coating over and/or inside it, e.g., it can have an interior lumen lined by PTFE to allow a line (e.g., a suture) to be atraumatically actuated through the lined lumen. As noted above, in some embodiments, after the pusher has pushed and properly positioned the ventricular coils of the anchoring device 1 in the left ventricle, the flexible portion 102 can be moved to release the atrial coils of the anchoring device 1 into the left atrium, while maintaining or holding a position of the ventricular coils of the anchoring device 1 within the left ventricle.

Once the anchoring device 1 is installed, the delivery catheter 100 can be removed by straightening or reducing the curvature of the flexible portion 102 to allow the delivery catheter 100 to pass back through the sheath 20. With the delivery catheter 100 removed, a prosthetic valve, for example, a prosthetic transcatheter heart valve (THV) 60 can then be passed, for example, through the sheath 20 and secured within the anchoring device 1, as shown for example in FIG. 2C. When the THV 60 is secured within the anchoring device 1, the sheath 20 along with any other delivery apparatuses for the THV 60 can then be removed from the patient's body and the openings in the patient's septum 55 and right femoral vein can be closed. In other embodiments, after the anchoring device 1 has been implanted, a different sheath or different delivery device altogether can be separately used to deliver the THV 60. For example, a guide wire can be introduced through sheath 20, or the sheath 20 can be removed and the guide wire can be advanced via the same access point, through the native mitral valve, and into the left ventricle, using a separate delivery catheter. Meanwhile, even though the anchoring device is implanted transseptally in this embodiment, it is not limited to transseptal implantation, and delivery of the THV 60 is not limited to transseptal delivery (or more generally via the same access point as delivery of the anchoring device). In still other embodiments, after transseptal delivery of the anchoring device 1, any of various other access points can thereafter be used to implant the THV 60, for example, trans-apically, trans-atrially, or via the femoral artery.

Figures 3, 4:
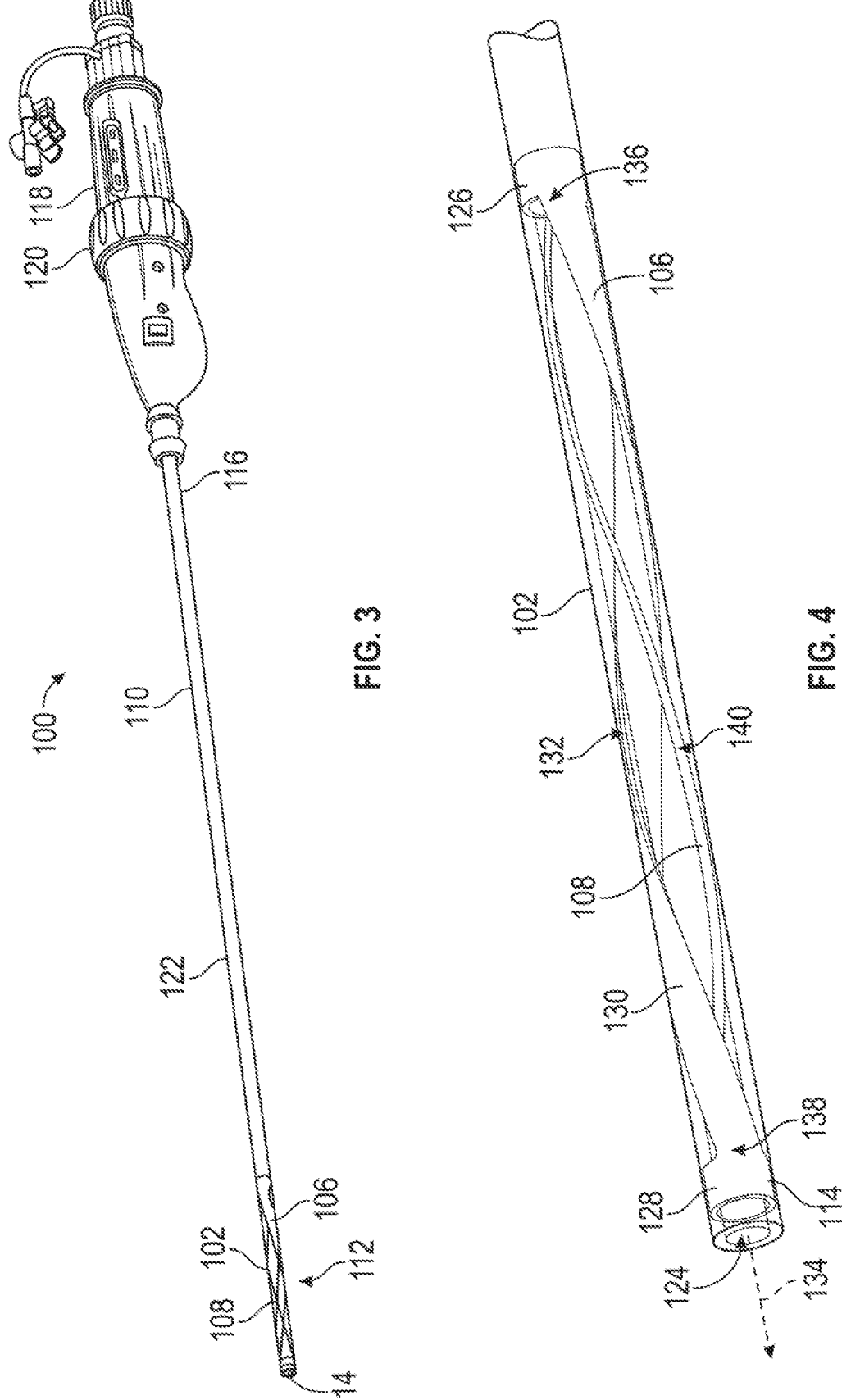
FIG. 3 shows a perspective view of a delivery catheter according to an embodiment of the present disclosure, with parts of a distal portion of the delivery catheter being transparent.
FIG. 4 shows a close up perspective view of a distal portion of the delivery catheter shown in FIG. 3, with parts of the distal portion being transparent.
Figures 5, 6A:
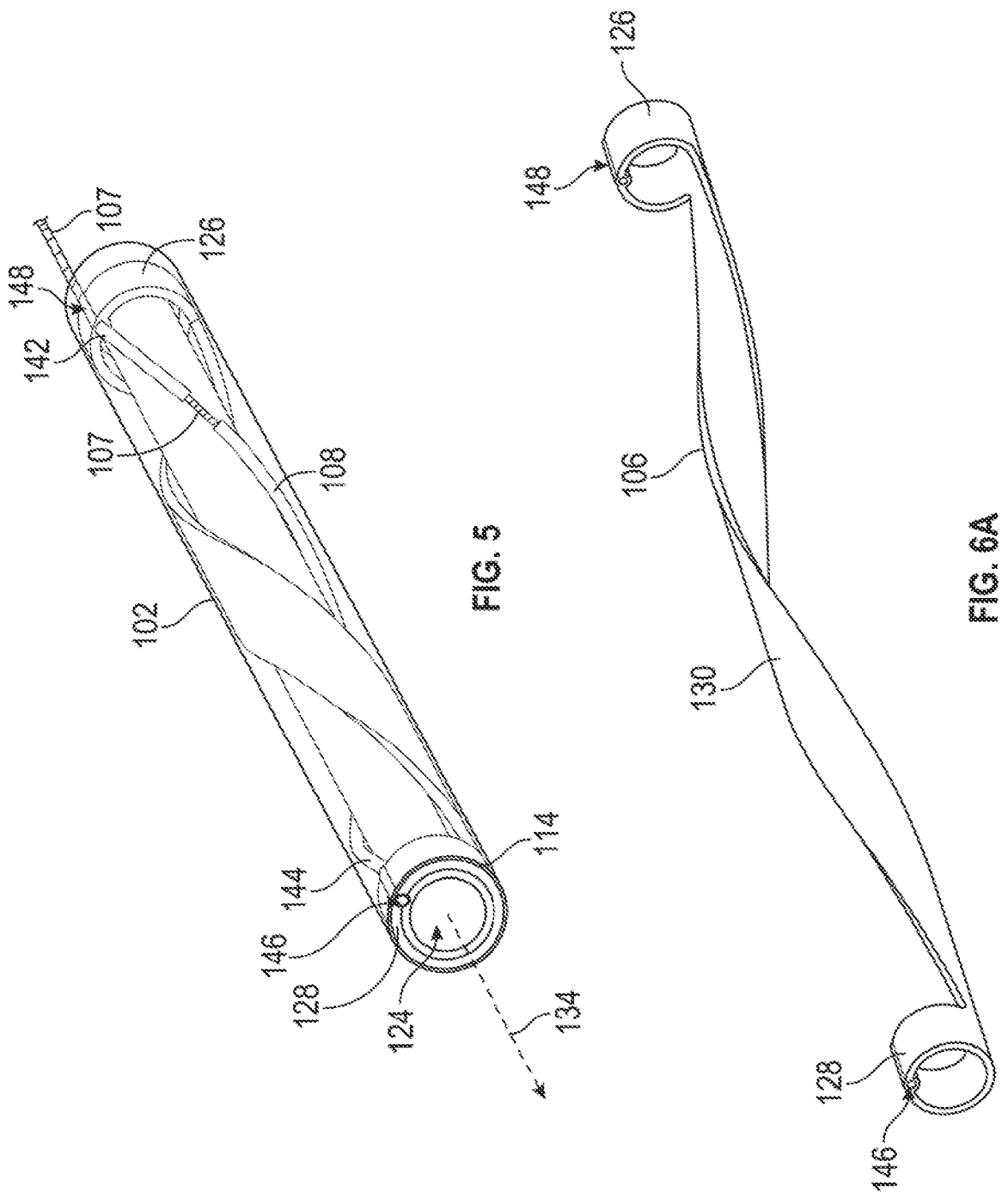
FIG. 5 shows a close up perspective view of a distal portion of a delivery catheter.
FIG. 6A shows a perspective view of a spine according to an embodiment of the present disclosure.

FIG. 3 shows a perspective view of a delivery catheter 100 that may be utilized according to embodiments herein. The flexible portion 102 is shown as partially transparent to show the position of a spine 106 and a tether channel 108 within the flexible portion 102. The tether channel 108 may be configured to receive a tether 107 (as shown in FIG. 5 for example). The delivery catheter 100 may include an elongate shaft 110 having a distal portion 112 with a distal tip 114. The elongate shaft 110 may include a proximal portion 116 that may couple to a handle 118.

The handle 118 may be configured for a user to grip and manipulate to control the elongate shaft 110. For example, the handle 118 may be configured for a user to grip as the elongate shaft 110 is advanced distally into vasculature of a patient's body. The handle 118 may further be configured for a user to grip to rotate the elongate shaft 110 when positioned within the patient's vasculature. Rotation of the handle 118 may rotate the position of the distal tip 114 of the elongate shaft 110 to place the distal tip 114 in a desired configuration.

The handle 118 may further include a deflection mechanism configured to move a tether 107 (marked in FIG. 5) that may extend within the tether channel 108. The deflection mechanism, for example, may include an actuator 120 that may be configured to be actuated by a user to move the tether within the tether channel 108. The actuator 120 may comprise a control knob as shown in FIG. 3, or in embodiments may have other forms. The actuator 120 may be configured to apply a longitudinal force to the tether within the tether channel 108 to move the tether within the tether channel 108. The longitudinal force may result in the flexible portion 102 of the elongate shaft 110 moving from a straightened shape as shown in FIG. 3 to a spiral shape as shown for example in FIG. 7C. In other embodiments, other forms of deflection mechanisms may be utilized.

The elongate shaft 110 may include an outer surface 122 that may be configured to slide within another catheter, such as the sheath 20 of the steerable guide sheath shown in FIG. 2B. The elongate shaft 110 may be configured to bend, for example, to contour to a shape of a sheath 20 of a sheath catheter or other structure that the elongate shaft 110 may pass through. The elongate shaft 110 may have a cylindrical shape, or may have another shape in embodiments as desired.

The elongate shaft 110 may comprise a sheath that an implant such as the anchoring device 1, along with other components of the implant delivery system, may be configured to pass through. The elongate shaft 110 may include an inner lumen 124 (marked in FIGS. 5 and 6C) that extends from the distal tip 114 of the elongate shaft 110 proximally to the proximal end of the elongate shaft 110. The inner lumen 124 may be configured for an implant such as the anchoring device 1 to be passed through. In embodiments, other components such as catheters or other devices may be passed through the inner lumen 124.

The flexible portion 102 may be positioned at the distal portion 112 of the elongate shaft 110. The flexible portion 102 is shown in partial transparent view in FIG. 3. The flexible portion 102 may be configured to form a spiral shape upon a longitudinal force being applied to a tether within the tether channel 108.

FIG. 4 shows a close up perspective view of the flexible portion 102 of the elongate shaft 110. A spine 106 and a tether channel 108 of the flexible portion 102 are shown in solid view with the remainder of the flexible portion 102 shown transparent. The spine 106 is shown to include a proximal ring 126 and a distal ring 128 and an elongate strip 130 extending between the proximal ring 126 and the distal ring 128. The elongate strip 130 may extend longitudinally in a spiral along a portion 132 of the flexible portion 102 that similarly extends in a spiral with the elongate strip 130.

Figure 6B:
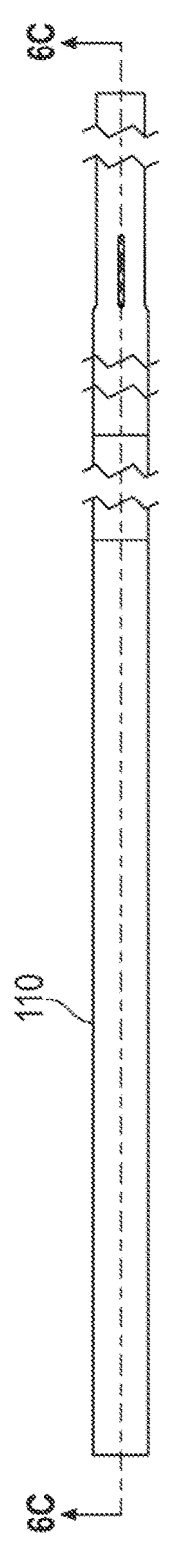
FIG. 6B shows a side view of an elongate shaft of a delivery catheter.
Figure 6C:
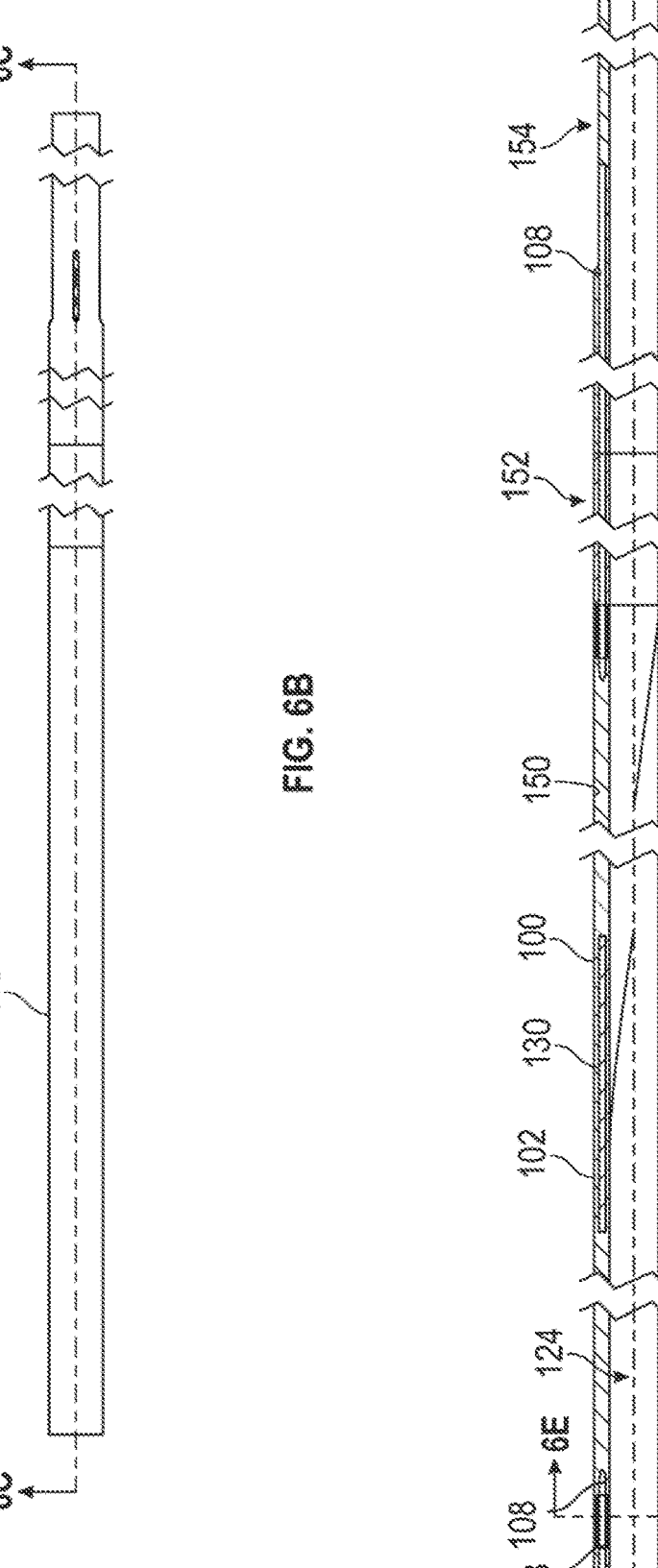
FIG. 6C shows a cross sectional view of the elongate shaft of the delivery catheter along line 6C-6C in FIG. 6B.
Figure 6D:
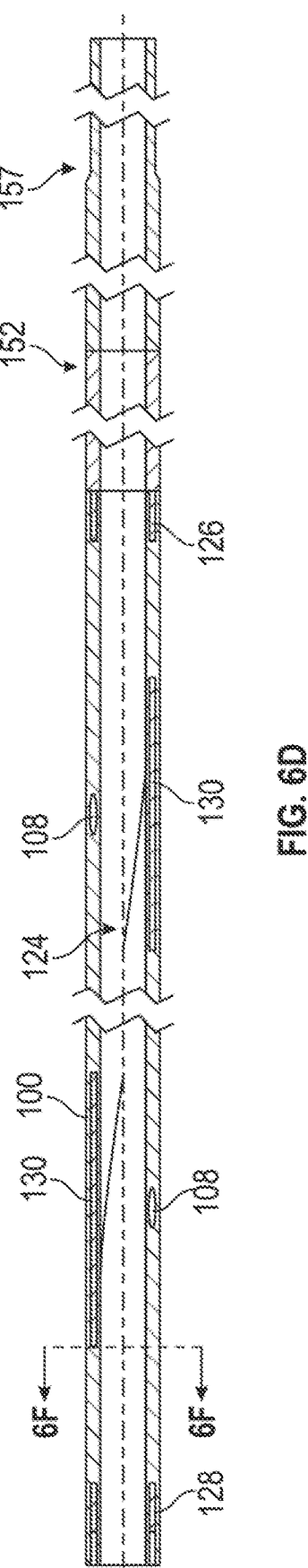
FIG. 6D shows a cross sectional view of the elongate shaft of the delivery catheter along line 6D-6D in FIG. 6E.
Figure 6F:
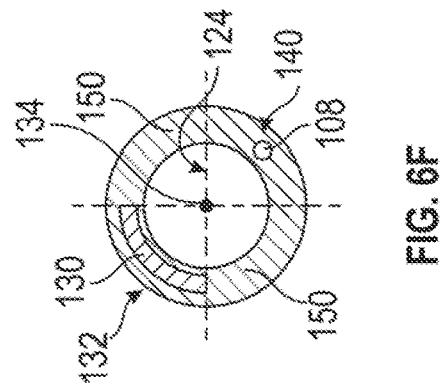
FIG. 6F shows a cross sectional view of the elongate shaft of the delivery catheter along line 6F-6F in FIG. 6D.

The elongate strip 130 may comprise a material that has less flexibility than circumferentially adjacent material 150 of the flexible portion 102 (shown in transparent view in FIG. 4 and marked in FIGS. 6C and 6F). As such, the elongate strip 130 may comprise a portion having a greater durometer than the circumferentially adjacent portions of the flexible portion 102 and the flexible portion 102 may be less prone to bend at the portion including the elongate strip 130.

Figure 11A:
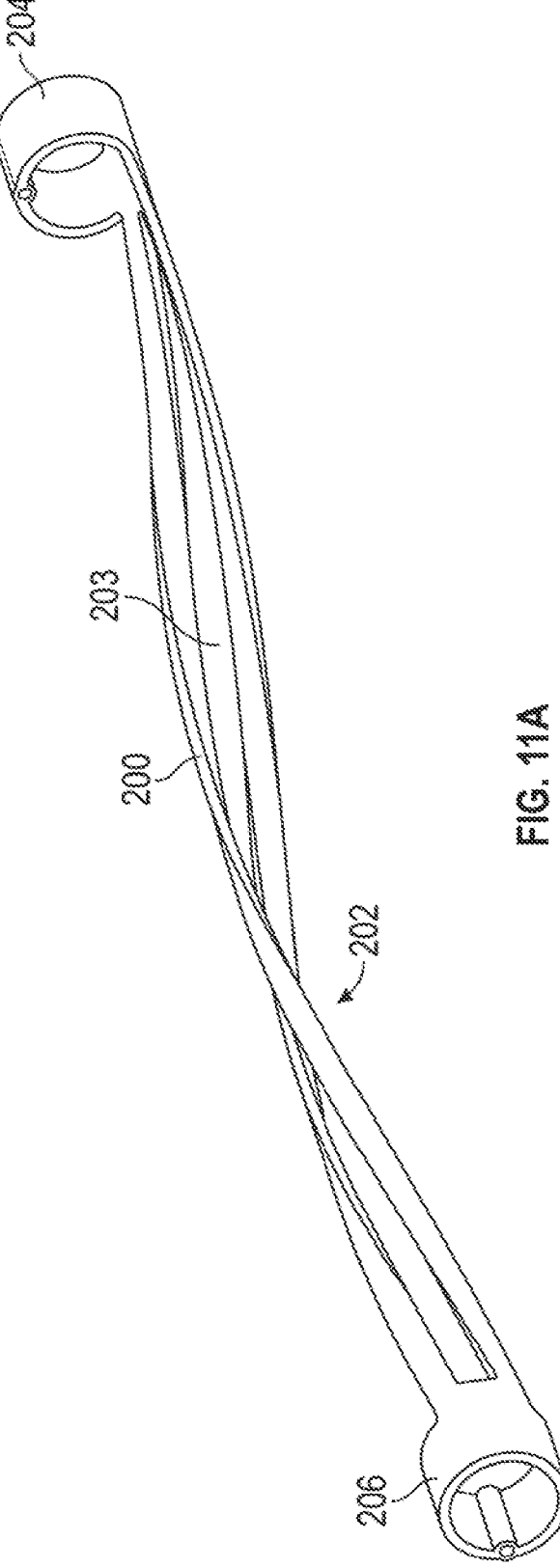
FIG. 11A shows a perspective view of a spine according to an embodiment of the present disclosure.
Figures 11B, 11C:
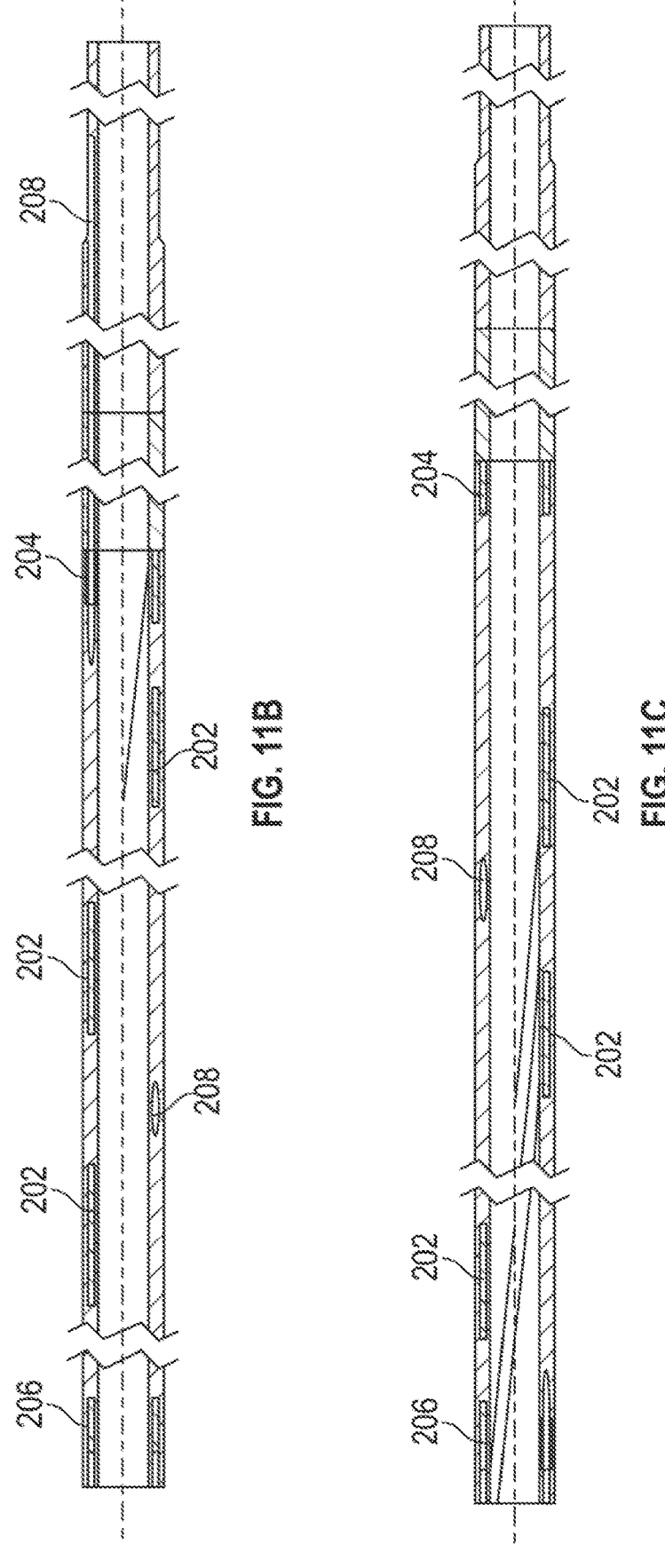
FIG. 11B shows a cross sectional view of an elongate shaft of a delivery catheter along a mid line.
FIG. 11C shows a cross sectional view of an elongate shaft of a delivery catheter along a view rotated 90 degrees from the view shown in FIG. 11B.

The elongate strip 130 as shown in FIG. 4, may comprise a single unitary body, although in embodiments the elongate strip 130 may have other configurations, including cut-out portions of the elongate strip 130. FIGS. 11A-C, for example, illustrate an embodiment including an elongate strip having a cut-out portion.

The elongate strip 130 as shown in FIG. 4 may form a spiral having a single full rotation about the longitudinal axis 134 of the lumen 124 and about the inner lumen 124. The coupling point 136 of the proximal end of the elongate strip 130 with the proximal ring 126, for example, may be at the same rotational orientation as the coupling point 138 of the distal end of the elongate strip 130 with the distal ring 128. In embodiments, other amounts of rotation about the longitudinal axis 134 of the lumen 124 may be utilized, such as shown in the embodiments of FIGS. 9A-12C.

The tether channel 108 may receive a tether 107 (marked in FIG. 5) that extends longitudinally in a spiral along another portion 140 of the flexible portion 102 that is circumferentially spaced from the portion 132. The tether channel 108 may similarly extend longitudinally in a spiral along the portion 140 of the flexible portion 102 that is circumferentially spaced from the portion 132. The tether and tether channel 108 may spiral at the same pitch as the elongate strip 130 and may spiral for the same rotational amount as the elongate strip 130 (e.g., a full rotation as shown in FIG. 4). The tether and tether channel 108 may spiral such that the portion 140 is positioned opposite from the portion 132 across the inner lumen 124 as the spiral continues along the length of the flexible portion 102. The elongate strip 130 and the tether channel 108 (including the tether 107) accordingly may form a double helix structure extending along the flexible portion 102. In embodiments, other positions of the tether and tether channel 108 may be utilized, including being positioned ninety degrees from the elongate strip 130 or another amount (e.g., 135 or 45 degrees or another amount of circumferential spacing as desired).

FIG. 5 shows a perspective view of the flexible portion 102 at a different angle of view than shown in FIG. 4. The tether channel 108 may include a proximal portion 142 (marked in FIG. 5) that may couple to the proximal ring 126. The tether channel 108 may further include a distal portion 144 (marked in FIG. 5) that couples to the distal ring 128. The tether channel 108 may couple to a coupling point 146 on the distal ring 128. The coupling point 146 may comprise a channel in the distal ring 128 for the tether channel 108 to pass through. The tether channel 108 may further couple to a similar coupling point 148 on a proximal ring 126.

A partial cut away view of the tether channel 108 is shown in FIG. 5, showing the tether 107 positioned within the tether channel 108. The tether 107 may have a distal portion coupled to the distal ring 128 and may extend proximally through the spiral tether channel 108 to exit the proximal ring 126 (as shown in FIG. 5 for example). The tether 107 may extend proximally to a proximal portion of the tether 107 that couples to a deflection mechanism of the handle or another system for applying a longitudinal force to the tether 107. The tether 107 may extend proximally from the proximal ring 126 through the elongate shaft and through a tether channel of the elongate shaft.

The tether 107 in embodiments may comprise a pull tether (such as a pull wire or another form of pull tether). The tether 107 may be configured to be retracted proximally to form the flexible portion 102 into a spiral shape. In embodiments, the tether 107 may be configured to form the flexible portion 102 into a spiral shape based on a distal force being applied to the tether 107. As such, the tether 107 may comprise a push rod or another material for transmitting the longitudinal force distally.

The tether 107 spirals along the tether channel 108 and accordingly extends longitudinally in the spiral along the portion 140 of the flexible portion 102 that is circumferentially spaced from the portion 132 of the elongate strip 130 (with the portions marked in FIGS. 4 and 6F). In embodiments, other configurations may be utilized.

The spine 106 and the tether channel 108 (and accordingly the tether 107) may each be embedded in material of the body of the flexible portion 102. The material 150 is transparent in FIG. 5, yet is visible in the cross sectional views of FIGS. 6C-6F. The material 150 may be less flexible and have a lower durometer than the material of the spine 106 and particularly the material of the elongate strip 130. FIG. 6F, for example, illustrates a cross sectional view showing that material may be positioned both radially inward and outward of the elongate strip 130 and the tether channel 108. As such, the material 150 may form an outer surface of the elongate shaft and an inner surface that faces the inner lumen 124. The material 150 may further be positioned circumferentially adjacent to the elongate strip 130 of the spine 106 and circumferentially adjacent to the tether channel 108 as shown in FIG. 6F.

The material 150 may comprise a material such as PEBAX or another material in embodiments as desired. The spine 106 may further comprise a PEBAX material, yet of a greater durometer than the material 150. Other materials may be utilized as desired.

The tether channel 108 may be configured as an embedded tube or may be configured as a cut-out portion of the body of the flexible portion 102. Other forms of channels may be utilized in embodiments.

FIG. 6B shows a side view of the elongate shaft 110. FIG. 6C shows a cross sectional view of the elongate shaft 110 along line 6C-6C in FIG. 6B. The elongate shaft 110 may include the spine 106 and the tether channel 108 each spiraling about the inner lumen 124.

In embodiments, a proximal portion of the spine 106 may couple to a passively flexible portion 152 of the elongate shaft 110. The passively flexible portion 152 may be configured to passively flex with the deflection of a sheath 20 of a sheath catheter (as shown in FIG. 2B). As such, a portion of the elongate shaft 110 proximal of the spine 106 may be configured to deflect with the sheath catheter or another mechanism in embodiments. The passively flexible portion 152 may comprise an intermediate portion of the elongate shaft between a flexible distal portion 102 and a proximal portion 154 of the elongate shaft 110. The passively flexible portion 152 may be positioned proximal of the proximal ring 126 of the spine 106. The proximal portion 154 of the elongate shaft 110 may be configured to couple to the handle 118.

The passively flexible portion 152 may have a lesser durometer than the durometer of the spine 106, yet may have a greater durometer than the material 150 of the flexible portion in embodiments. The passively flexible portion 152 may include a material such as PEBAX, although other materials may be utilized as desired.

Figure 6E:
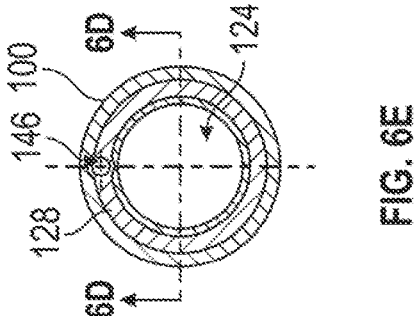
FIG. 6E shows a cross sectional view of the elongate shaft of the delivery catheter along line 6E-6E in FIG. 6C.

FIG. 6D shows a cross sectional view of the elongate shaft 110 at a view rotated 90 degrees from the view shown in FIG. 6C (and marked as line 6D-6D in FIG. 6E). The corresponding spiral rotation of the elongate strip 130 and the tether channel 108 are shown.

FIG. 6E shows a cross sectional view of the elongate shaft 110 alone line 6E-6E in FIG. 6C. The distal ring 128 is shown embedded in material of the elongate shaft 110.

FIG. 6F shows a cross sectional view of the elongate shaft 110 along line 6F-6F in FIG. 6D. The position of the elongate strip 130 is shown positioned opposite the position of the tether channel 108. The tether channel 108 may be positioned opposite the center of the elongate strip 130 in embodiments. The opposed position continues as the elongate strip 130 and tether channel 108 rotate together in a spiral about the longitudinal axis 134 of the elongate shaft 110.

The spiral shape of the spine 106 and the tether channel 108 may allow the flexible portion 102 to form a spiral shape upon a longitudinal force being applied to the tether.

Figure 7A:
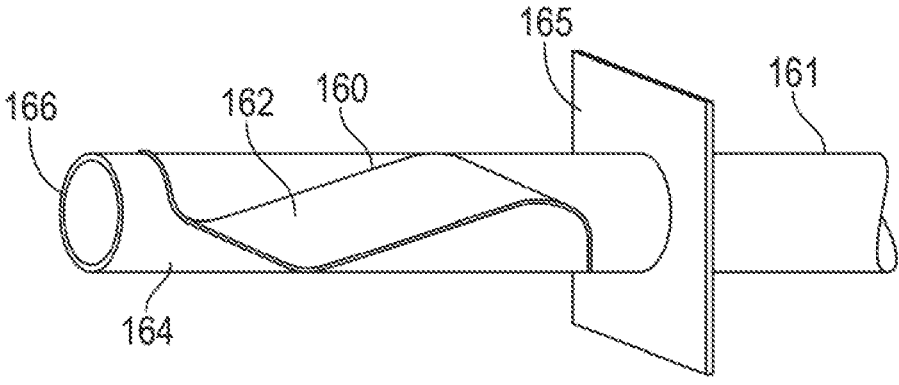
FIG. 7A shows a schematic view of a flexible portion of a delivery catheter.
Figure 7B:
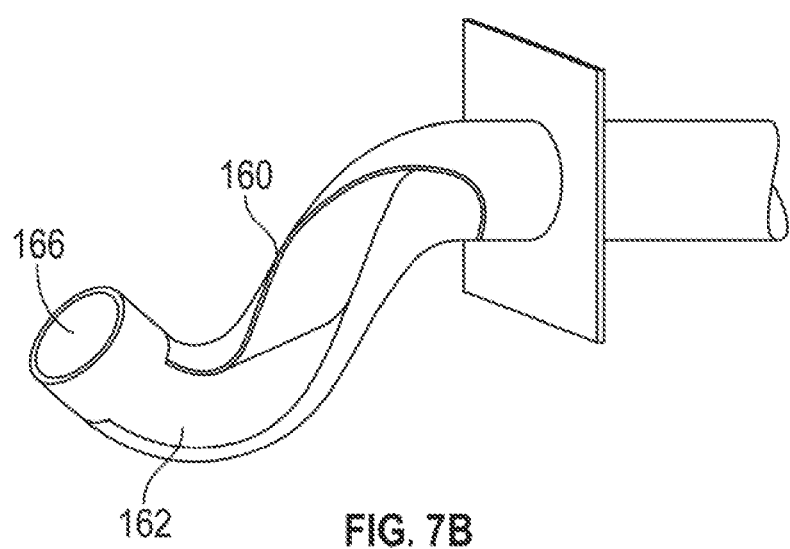
FIG. 7B shows a schematic view of the flexible portion of the delivery catheter shown in FIG. 7A flexed from the position shown in FIG. 7A.
Figure 7C:
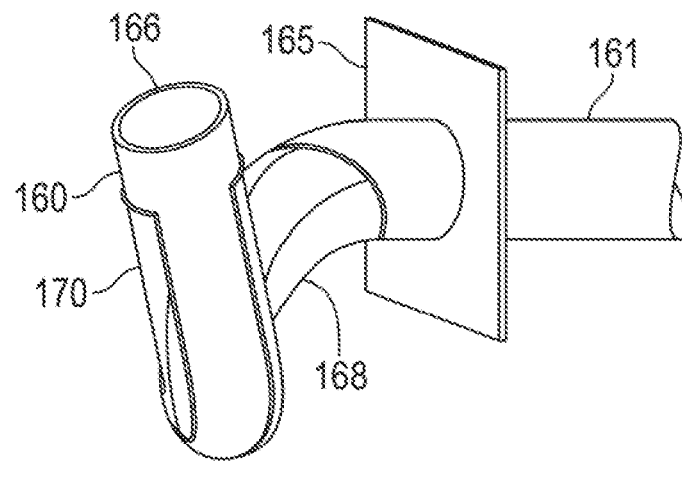
FIG. 7C shows a schematic view of the flexible portion of the delivery catheter shown in FIG. 7B flexed from the position shown in FIG. 7B.

FIGS. 7A-7C illustrate a schematic view of a flexible portion 160 of a delivery catheter including a spiral spine 162 and a spiral tether as shown in the embodiment of FIGS. 3-6F for example. The spiral tether is excluded from view in FIGS. 7A-7C. The direction of rotation of the spiral spine 162 is clockwise with respect to the proximal portion 161 of the elongate shaft 164 (as opposed to counter-clockwise in the embodiment of FIGS. 3-6F), yet a similar movement of the elongate shaft to a spiral shape may occur with the embodiment of FIGS. 7A-7C as with FIGS. 3-6F (although in a different direction). Further, the spiral spine 162 shown in FIGS. 7A-7C has a half rotation (and the embodiment of FIGS. 3-6F has a full rotation), yet the resulting spiral shape of the flexible portion 160 may be similar as with a spine with a full rotation.

The shape shown in FIG. 7A may be a straightened shape for the flexible portion 160, in which the flexible portion 160 has not yet been bent into a spiral shape. The distal tip 166 may be oriented perpendicular to a plane 165 that a portion of the elongate shaft 164 proximal of the spiral passes perpendicular through. As shown in FIG. 7B, with the tension in the tether increasing, the flexible portion 160 may start to bend. The flexible portion 160 may move from a straightened shape to a spiral shape. The spine 162 may form an outer curve of the flexible portion 160, with the tether (not shown in FIGS. 7A-7C, yet may be positioned in the same location as shown in FIG. 5 for example) forming an inner curve. The orientation of the distal tip 166 may start to deflect from the orientation shown in FIG. 7A. The direction of the distal tip 166 may vary from the direction shown in FIG. 7A.

As the tension in the tether increases, the flexible portion 160 reaches the spiral shape shown in FIG. 7C. The flexible portion 160 forms an upper curve portion 168 and a lower curve portion 170 that is positioned distal of the upper curve portion 168. The curvature of the upper curve portion 168 and the lower curve portion 170 may be similar, or may be different in embodiments. The spiral shape of the flexible portion 160 may be helical.

The distal tip 166 may be oriented to extend transverse to the orientation of the proximal portion 161 of the elongate shaft 164. The distal tip 166 may be oriented substantially parallel to the plane 165 that the portion of the elongate shaft 164 proximal of the spiral passes perpendicular through.

The lower curve portion 170 may be set to extend in a plane that is at or parallel with the plane of the native valve to which the elongate shaft 164 is proximate. As such, the distal tip 166 may be configured to deploy an implant, such as an anchoring device 1, in a plane that is at the plane of the native valve (such as a native mitral valve).

The flexible portion 160 may further be configured to bend to move from the spiral shape shown in FIG. 7C back to the straightened shape shown in FIG. 7A. Such a configuration may allow the elongate shaft 164 to be retracted from a portion of the patient's body following deployment.

Various sheath and delivery catheter designs can be used to effectively deploy the anchoring device at the implant site. For example, for deployment at the mitral position, the delivery catheter can be shaped and/or positioned to point towards commissure A3P3, so that a coil anchor deployed from the catheter can more easily enter the left ventricle and encircle the chordae 62 during advancement. However, while the various exemplary embodiments of the invention described below are configured to position the distal opening of the delivery catheter at commissure A3P3 of the mitral valve, in other embodiments, the delivery catheter can approach the mitral plane to point to, and the anchoring device can be advanced through, commissure A1P1 instead. In addition, the catheter can bend either clockwise or counter-clockwise to approach either commissure of the mitral valve or a desired commissure of another native valve, and the anchoring device can be implanted or inserted in a clockwise or counter-clockwise direction (e.g., coils/turns of the anchoring device can turn in a clockwise or counter-clockwise direction depending on how the anchoring device will be implanted).

In still further embodiments, the delivery catheter itself can also be positioned to pass below a plane of the annulus of a native valve and sit in one of the commissures or to extend into a ventricle (e.g., through one of the commissures). In some embodiments, the distal end of the delivery catheter can even be used to capture and/or corral some or all the chordae tendineae 62. The delivery catheter can be positioned in any suitable manner that allows an anchoring device to be deployed at an implant site. In some embodiments, the delivery catheter itself can have an atraumatic distal tip design, to provide atraumatic access to the implant site, for example, by reducing or eliminating any damage that could potentially be caused by the advancement and/or shape manipulation of the catheter while it is positioned at the implant site.

Figures 8A, 8B:
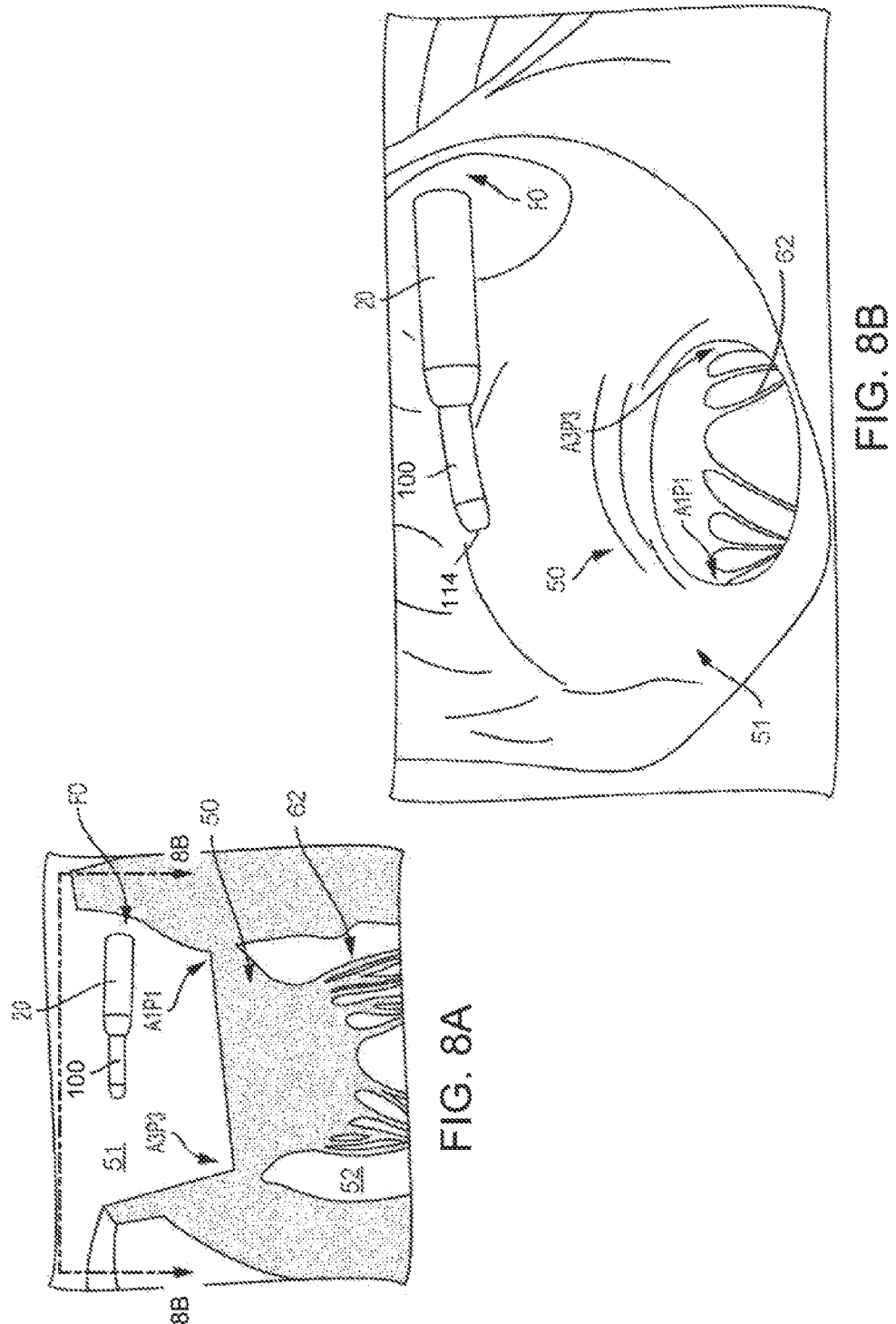
FIG. 8A is a side cutout view of a portion of a patient's heart that illustrates an exemplary delivery catheter entering the left atrium through the fossa ovalis in an exemplary method.
FIG. 8B illustrates the delivery catheter of FIG. 8A entering the left atrium of the patient's heart in the position shown in FIG. 8A, in which the delivery device is shown from a view taken along the lines 8B-8B in FIG. 8A.
Figure 8C:
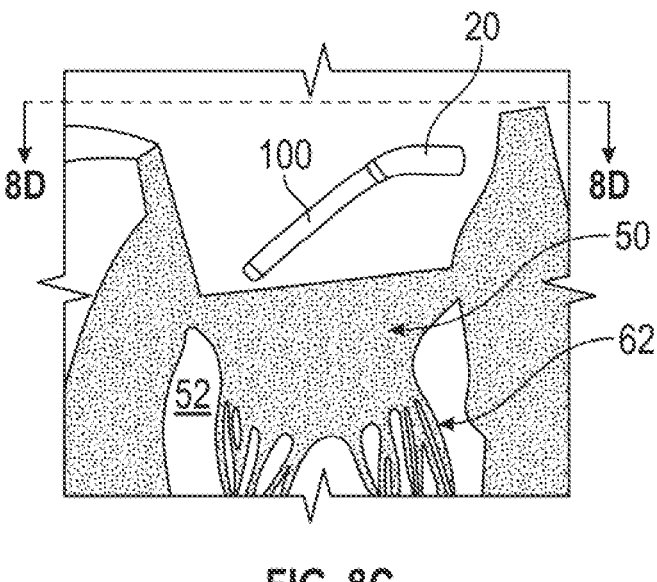
FIG. 8C illustrates the delivery catheter of FIG. 8A in a second position.
Figure 8D:
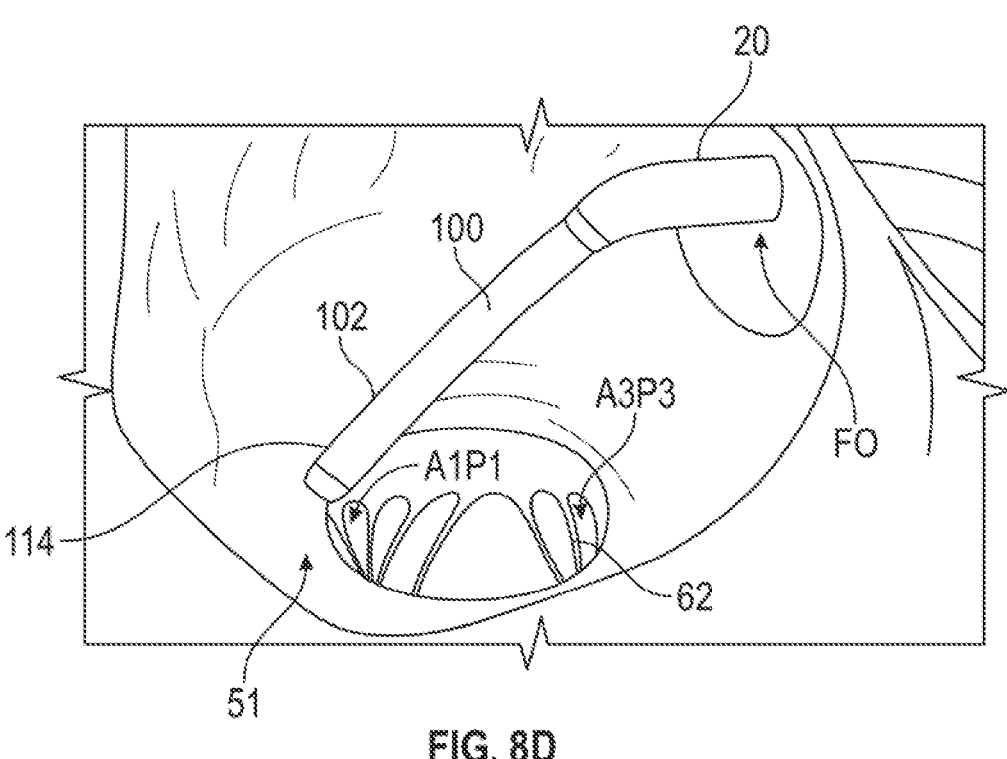
FIG. 8D illustrates the delivery catheter of FIG. 8A in the second position shown in FIG. 8C, in which the delivery catheter is shown from a view taken along the lines 8D-8D in FIG. 8C.
Figure 8E:
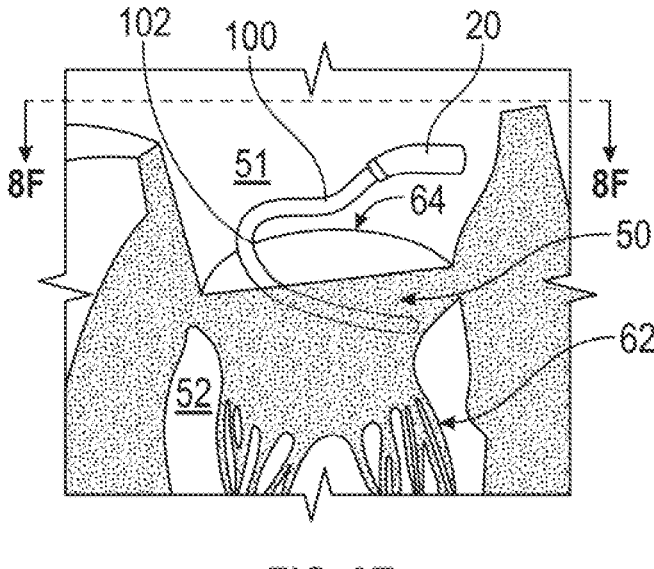
FIG. 8E illustrates the delivery device of FIG. 8A in a third position.
Figure 8F:
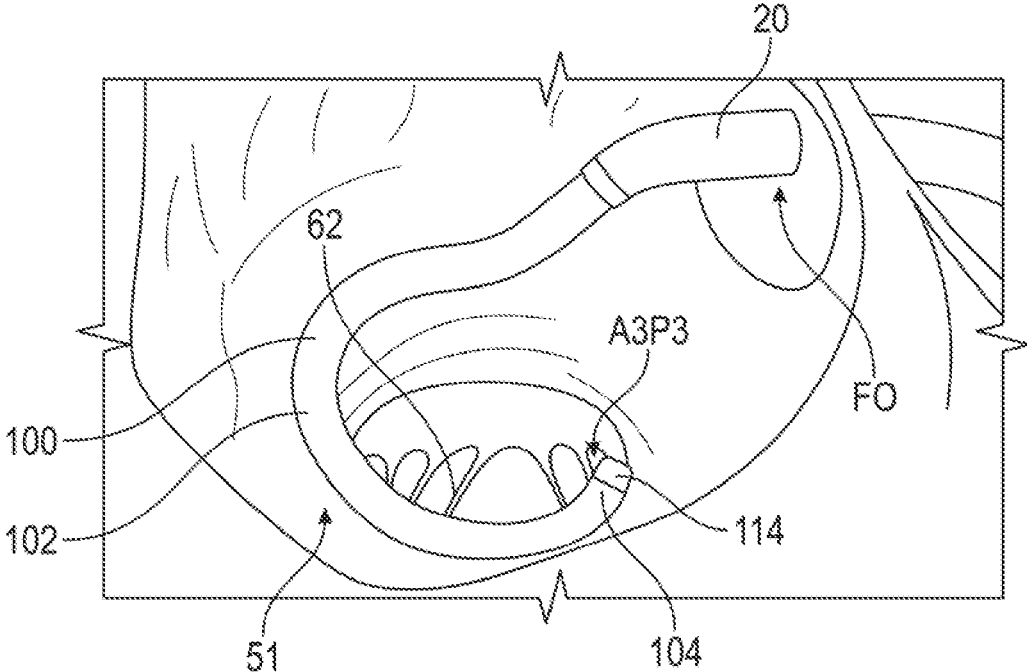
FIG. 8F illustrates the delivery device of FIG. 8A in the fourth position shown in FIG. 8E, in which the delivery device is shown from a view taken along the lines 8F-8F in FIG. 8E.
Figure 8G:
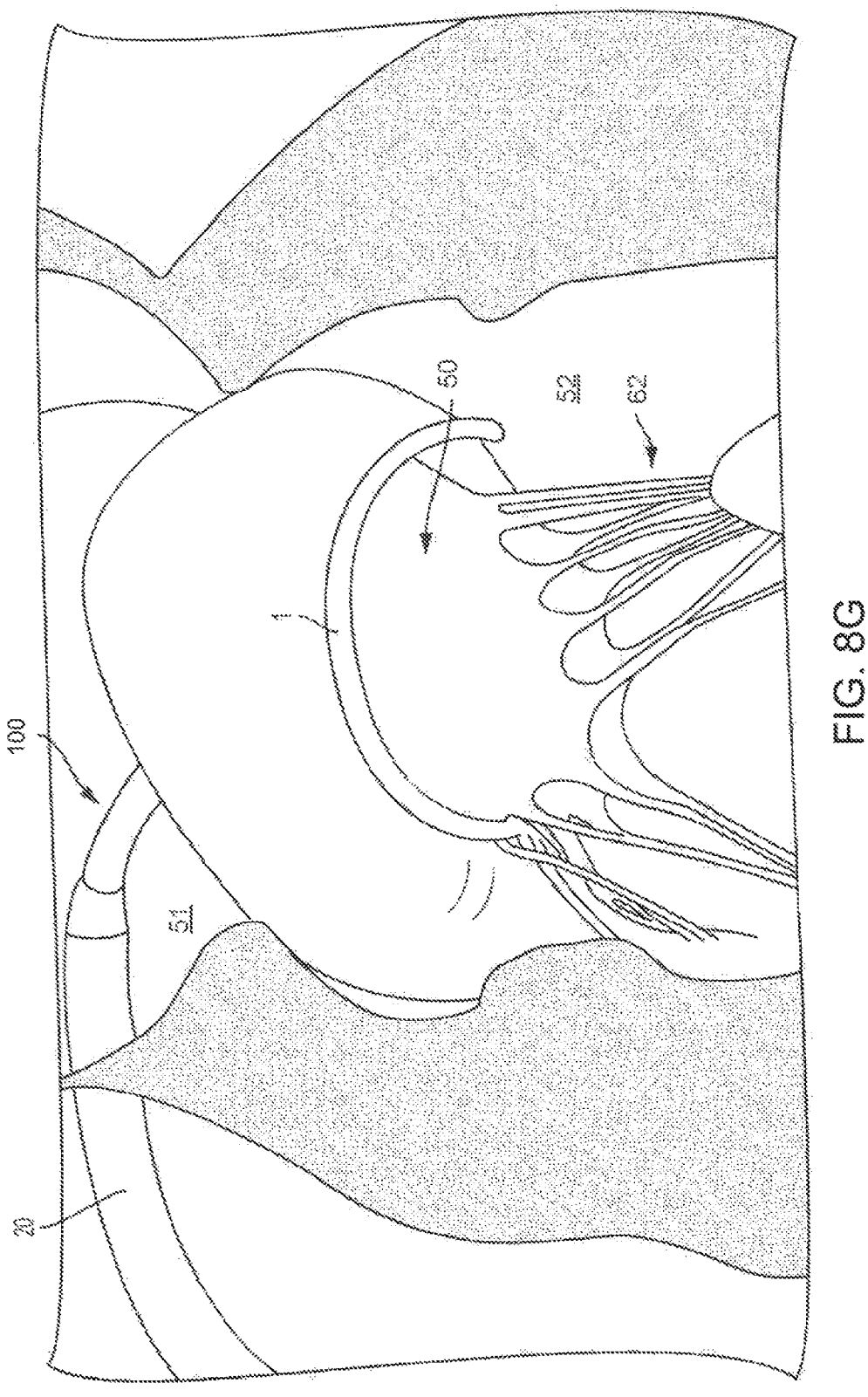
FIG. 8G is a side cutout view of the left side of a patient's heart that illustrates an anchoring device being delivered around the chordae tendineae and leaflets in the left ventricle of the patient's heart.
Figure 8H:
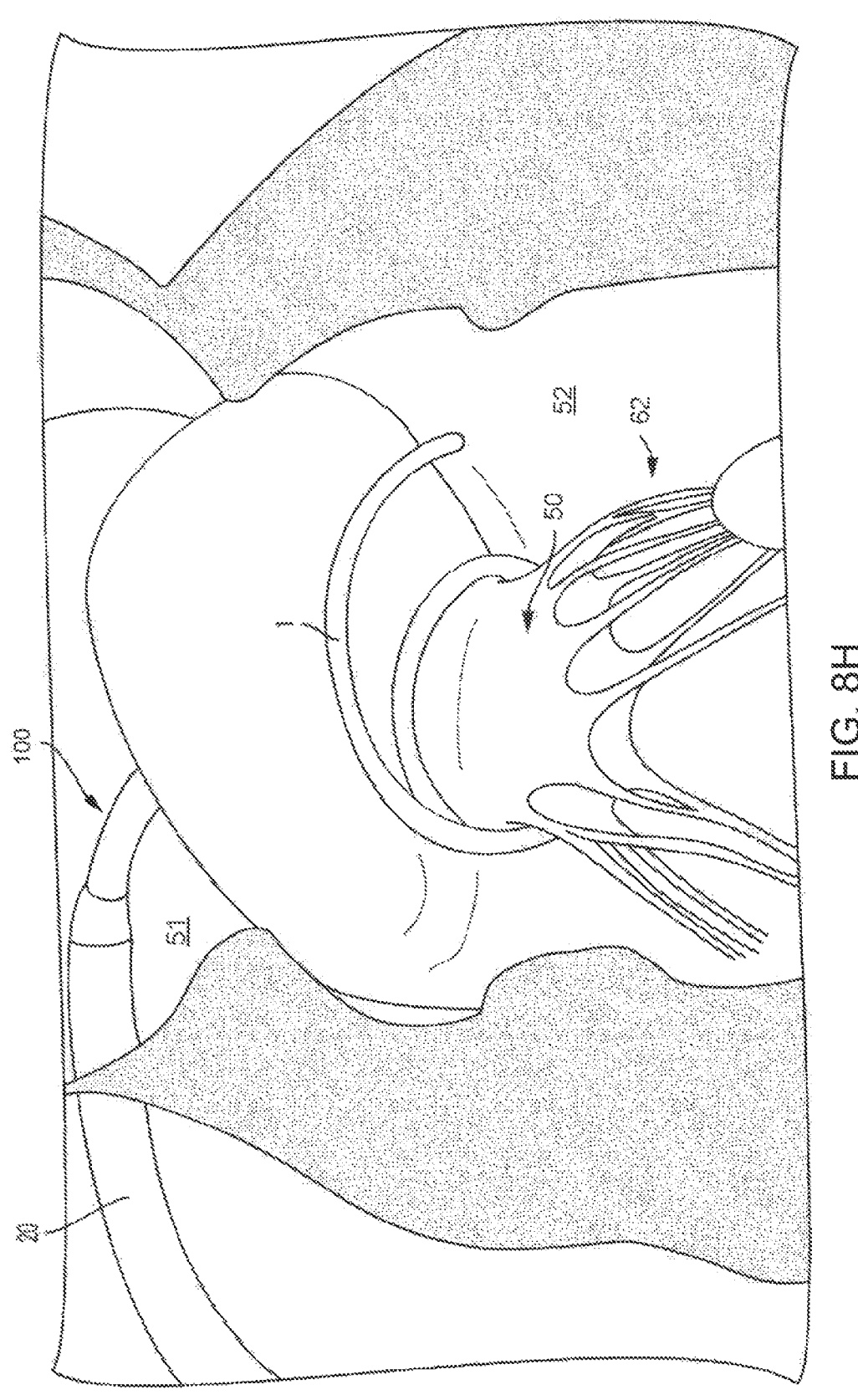
FIG. 8H illustrates the anchoring device of FIG. 8G further wrapping around the chordae tendineae and leaflets in the left ventricle of the patient's heart as it is being delivered by the delivery catheter of FIG. 8A.
Figure 81:
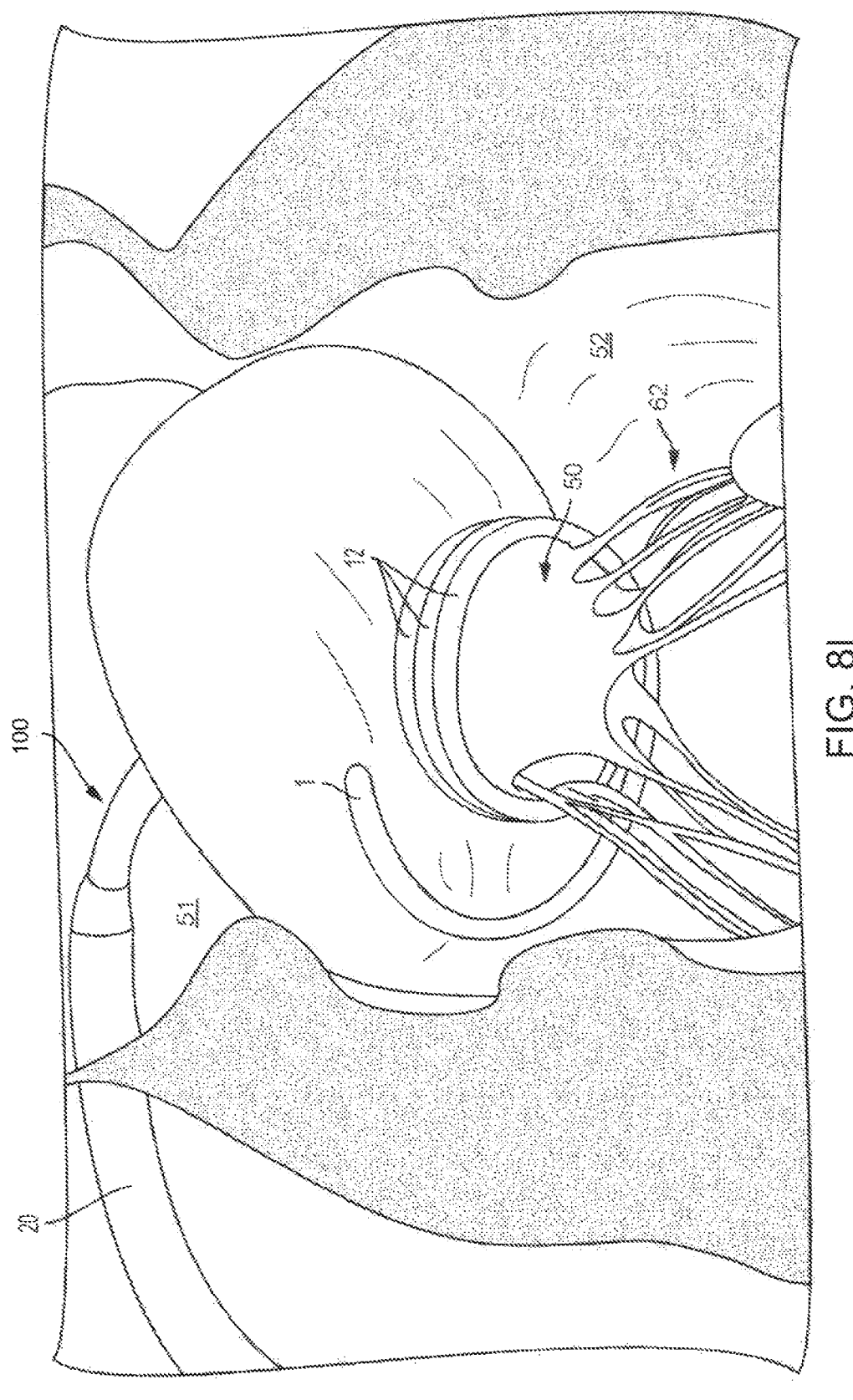
Figure 8J:
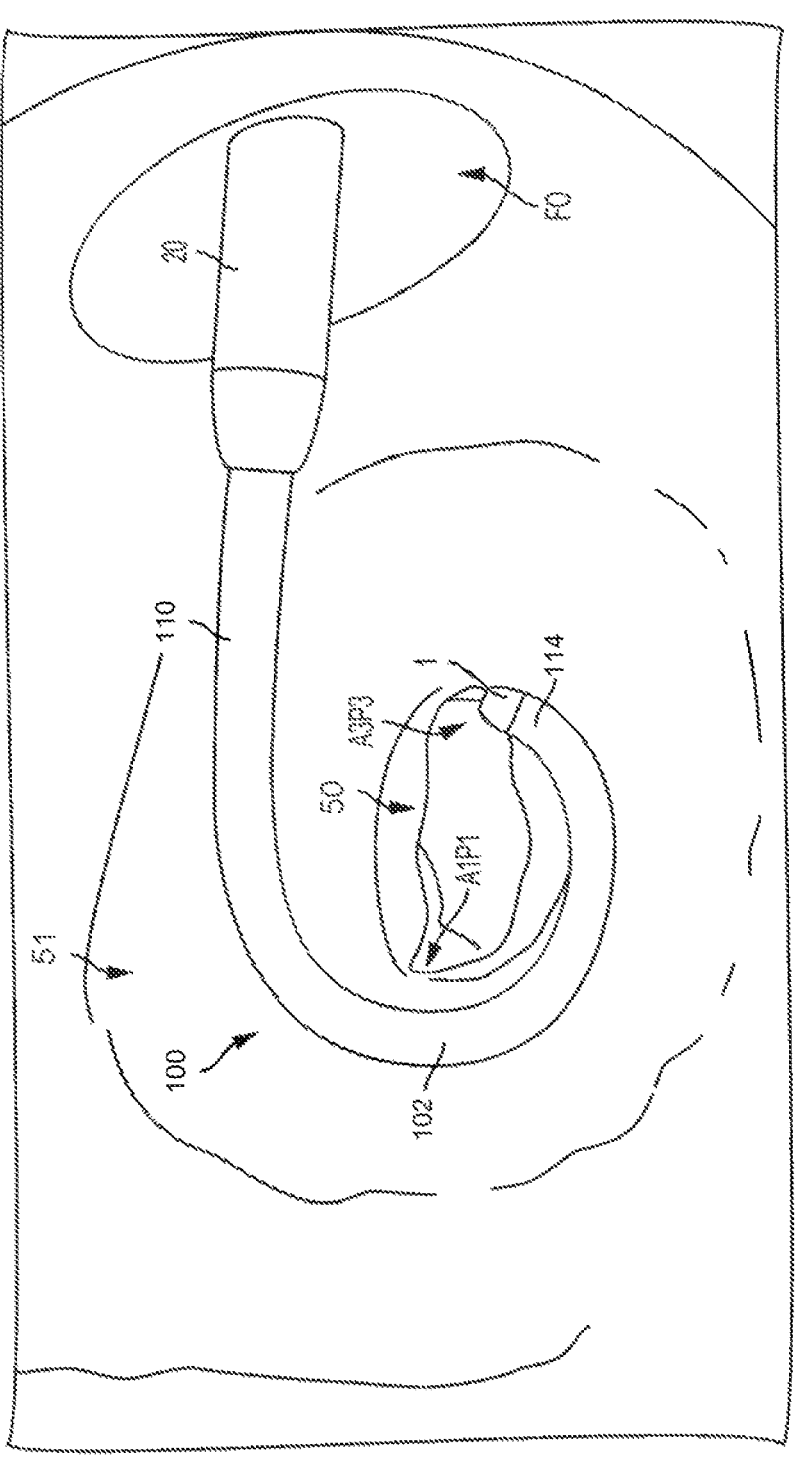
FIG. 8J is a view looking down into the patient's left atrium, illustrating the delivery catheter of FIG. 8A, after the anchoring device of FIG. 8G is wrapped around the chordae tendineae and leaflets in the left ventricle of the patient's heart.
Figure 8K:
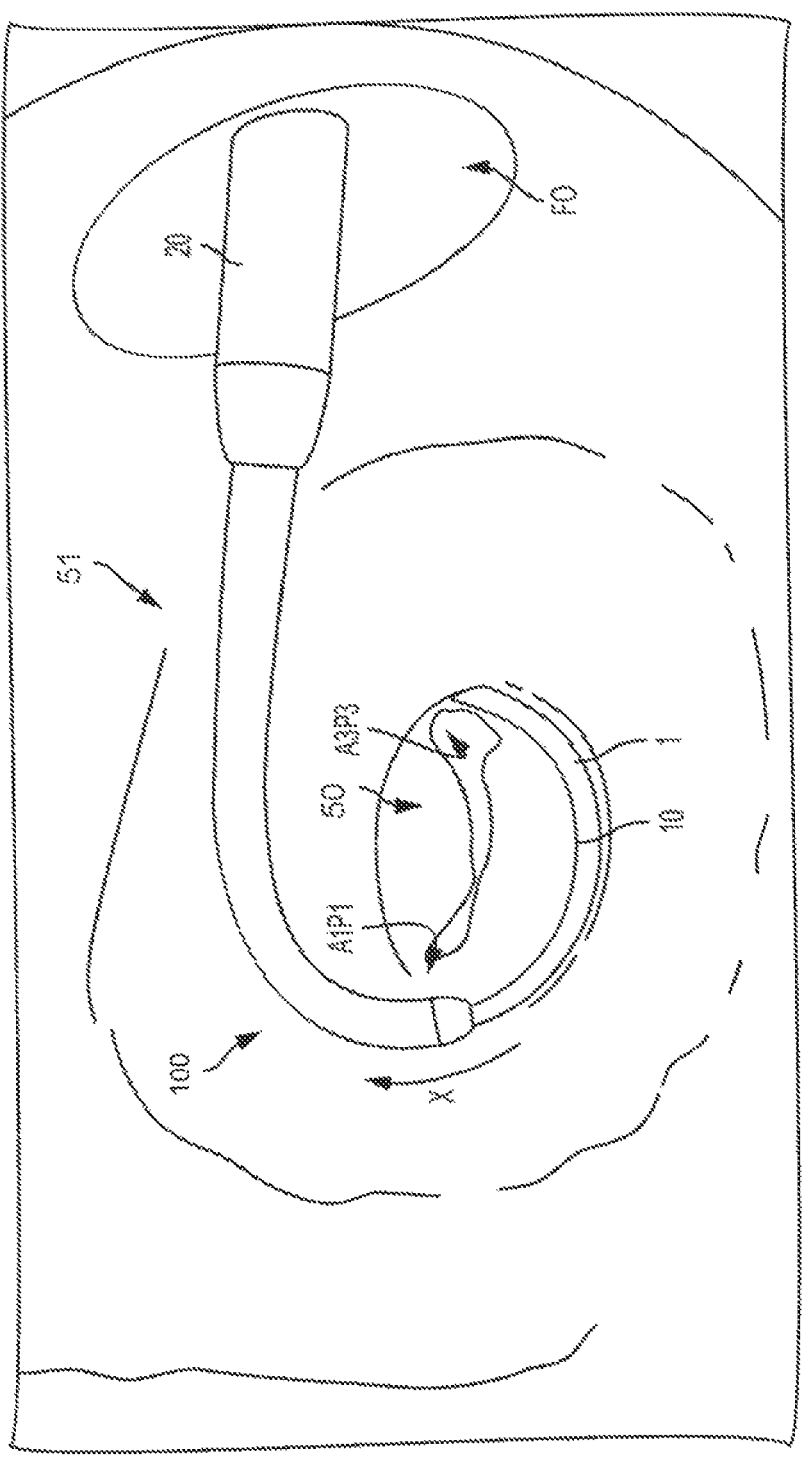
FIG. 8K illustrates the delivery catheter of FIG. 8A in the left atrium of the patient's heart, in which the delivery catheter is retracting to deliver a portion of the anchoring device in the left atrium of the patient's heart.
Figure 8L:
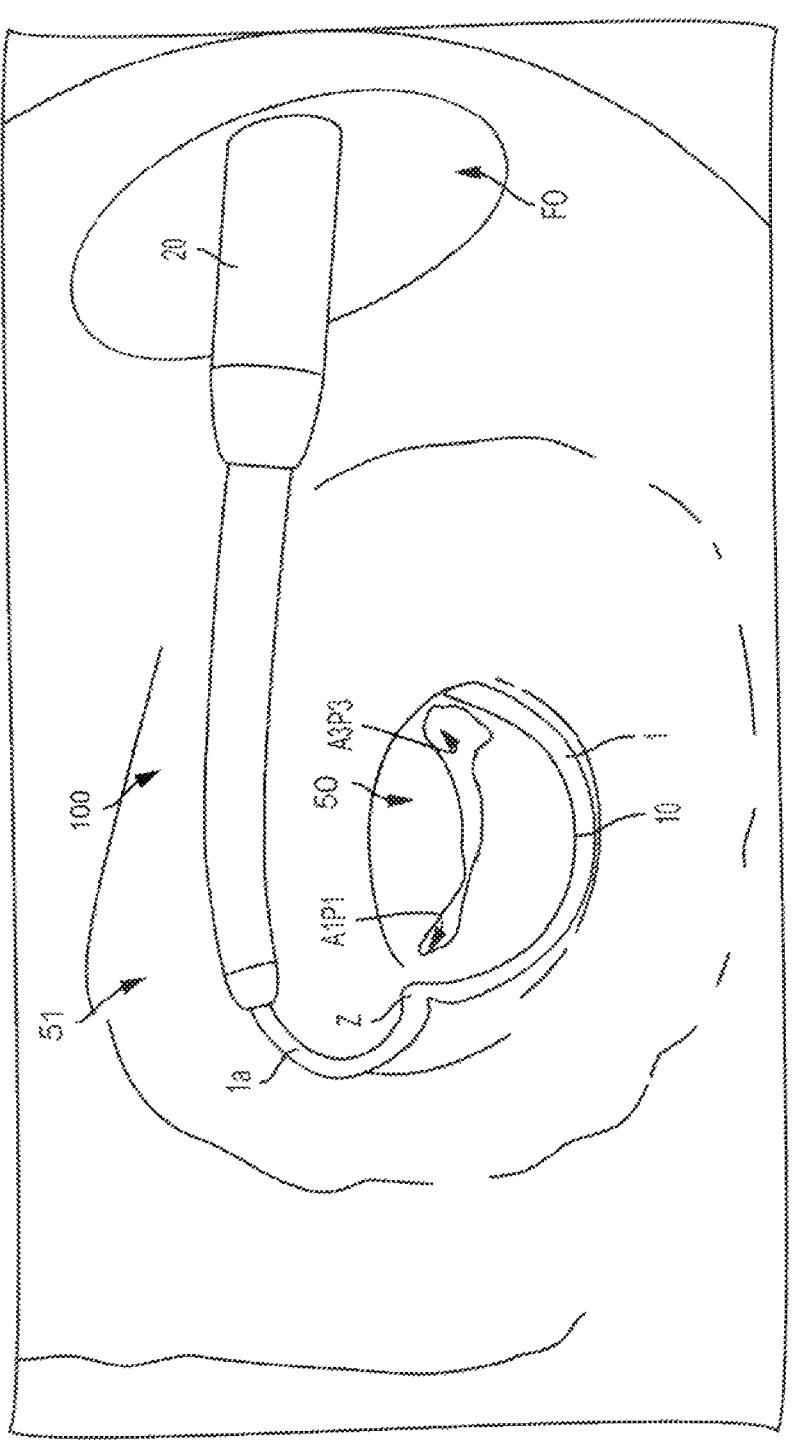
FIG. 8L illustrates the delivery catheter of FIG. 8A in the left atrium of the patient's heart, in which the delivery catheter is retracting to deliver a further portion of the anchoring device in the left atrium of the patient's heart.
Figure 8M:
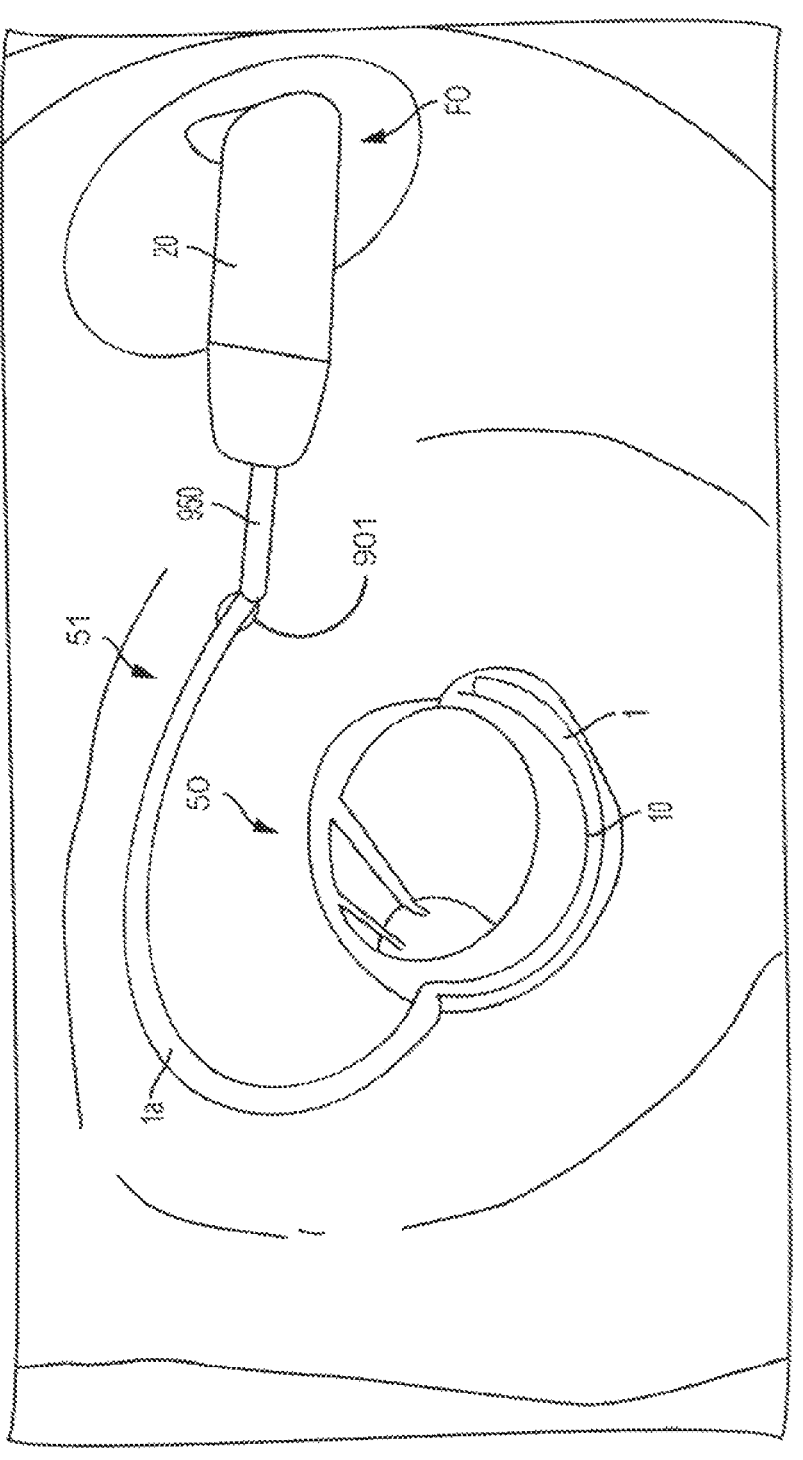
FIG. 8M illustrates the delivery catheter of FIG. 8A in the left atrium of the patient's heart, in which the anchoring device is exposed and shown connected tightly to a pusher in the left atrium of the patient's heart.
Figure 8N:
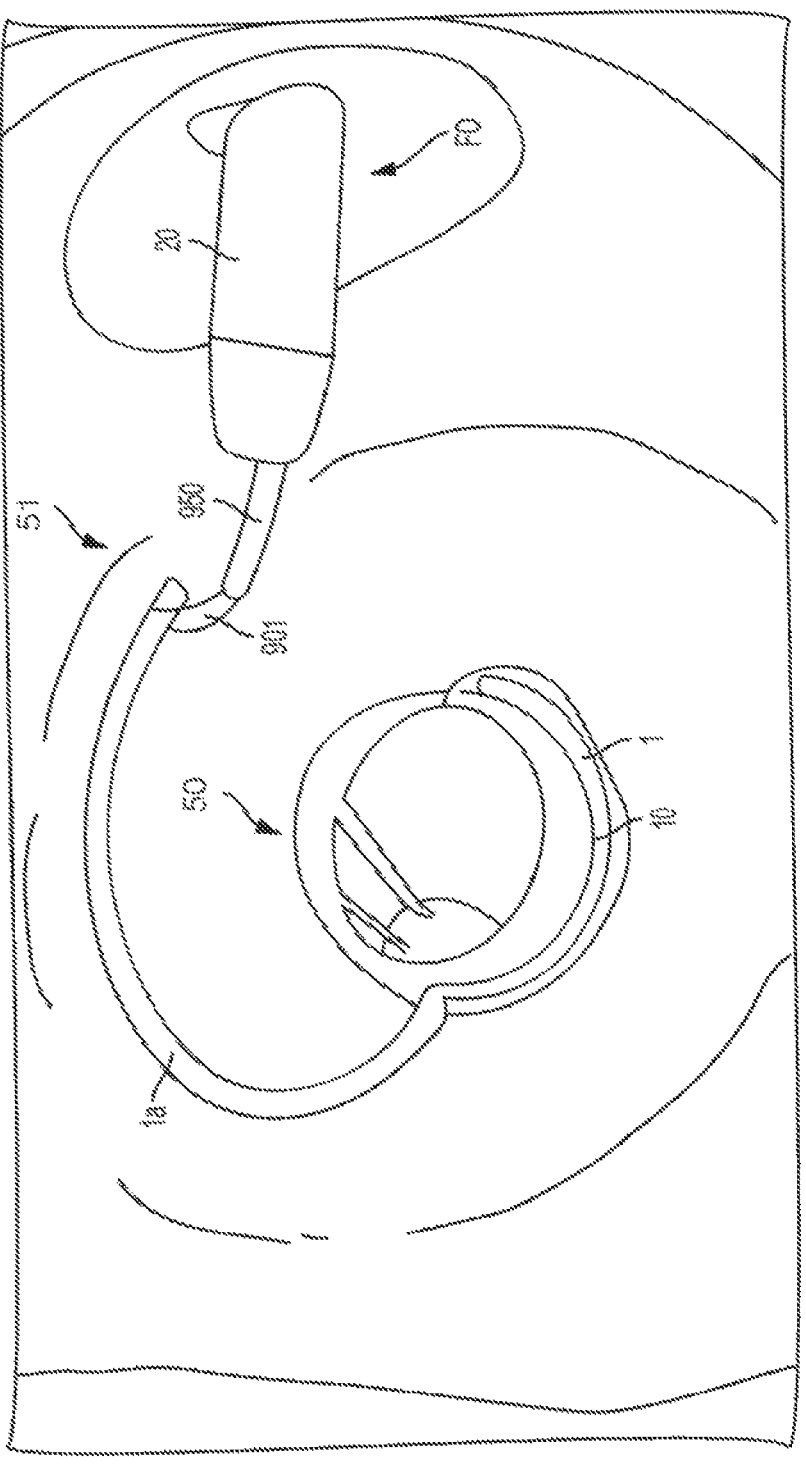
FIG. 8N illustrates the delivery catheter of FIG. 8A in the left atrium of the patient's heart, in which the anchoring device is fully removed from the delivery device and is loosely and removably attached to the pusher by a suture.
Figure 80:
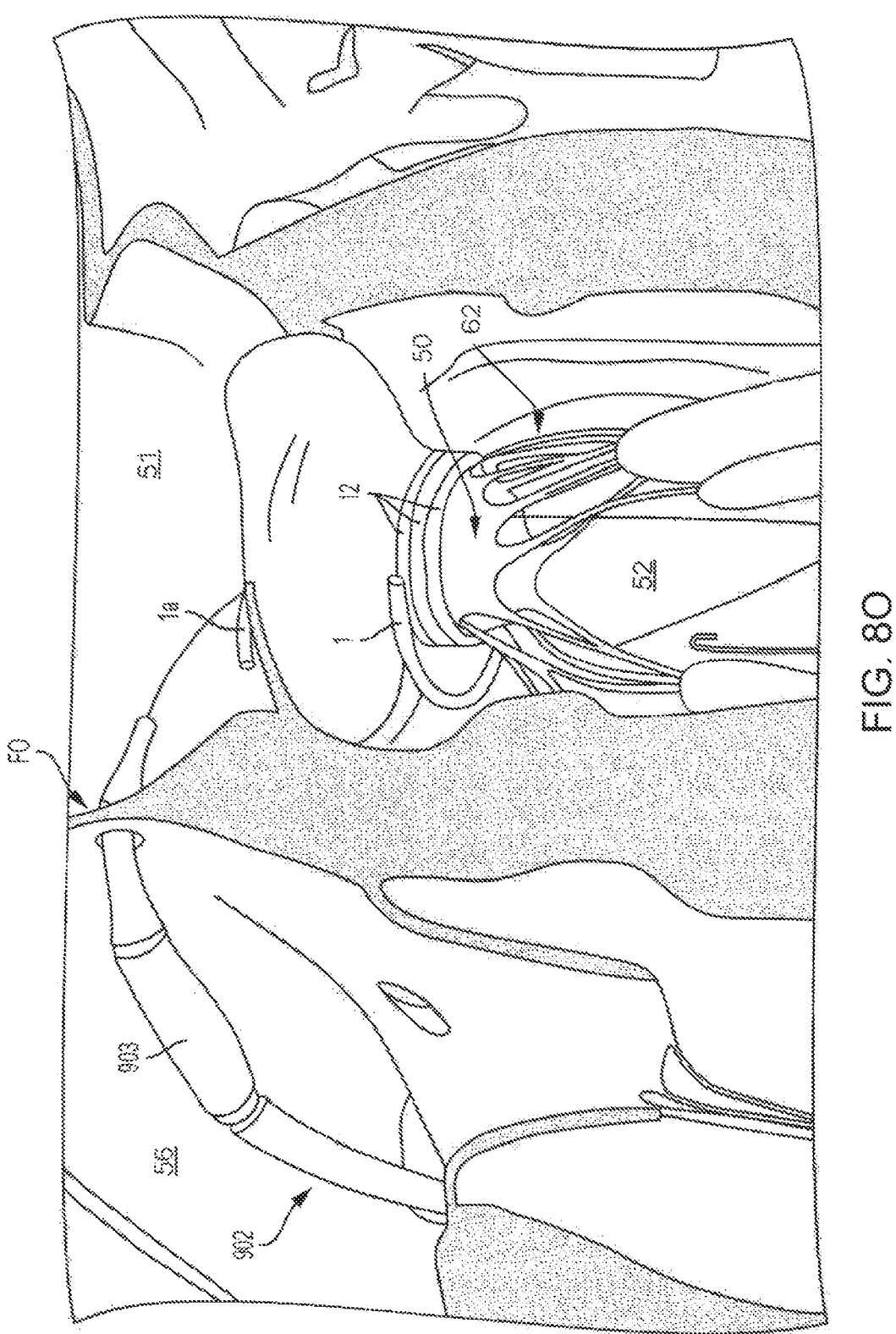
Figure 8P:
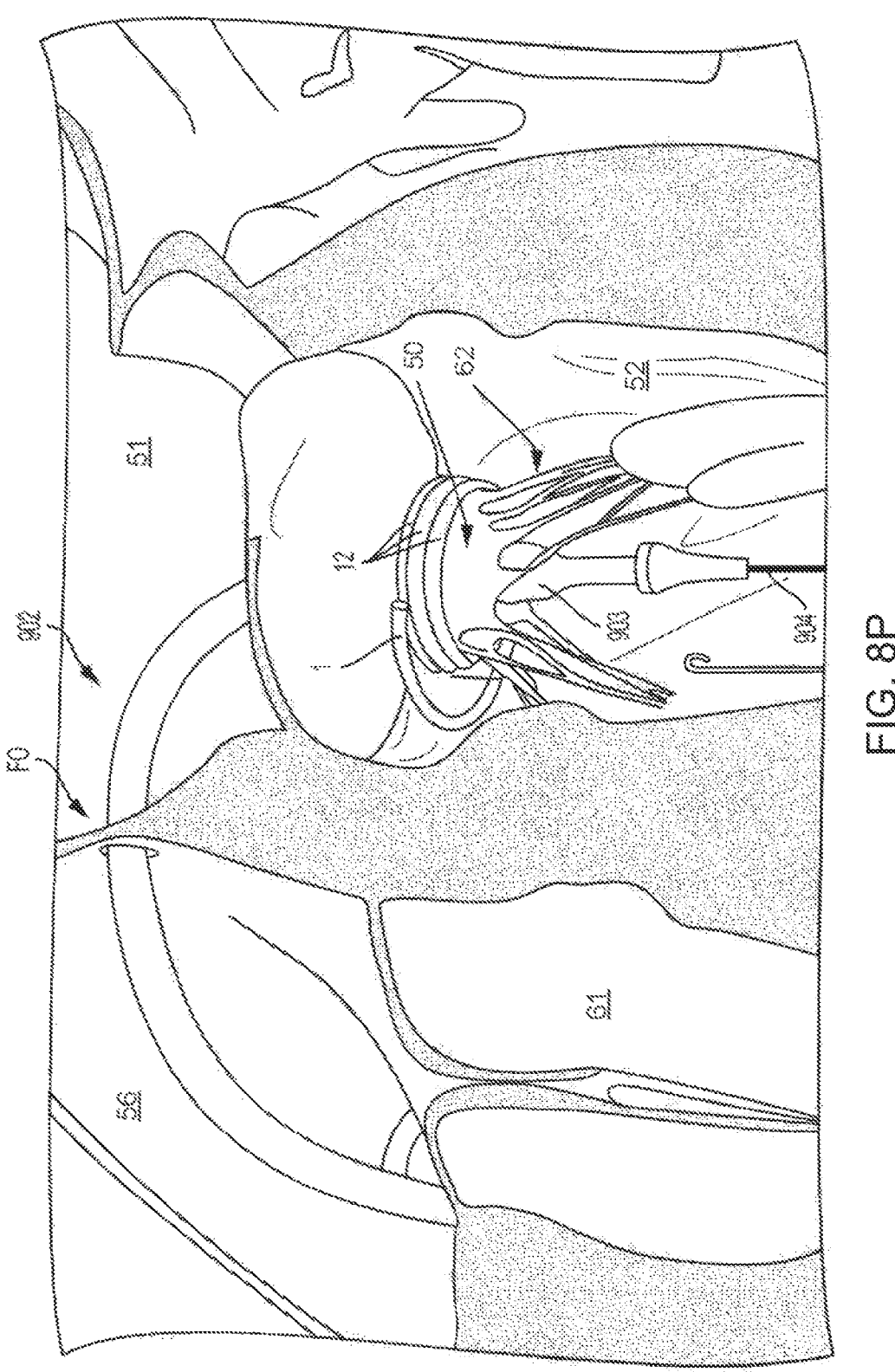
FIG. 8P illustrates the heart valve of FIG. 8O being further delivered to the mitral valve of the patient by the heart valve delivery device.
Figure 8Q:
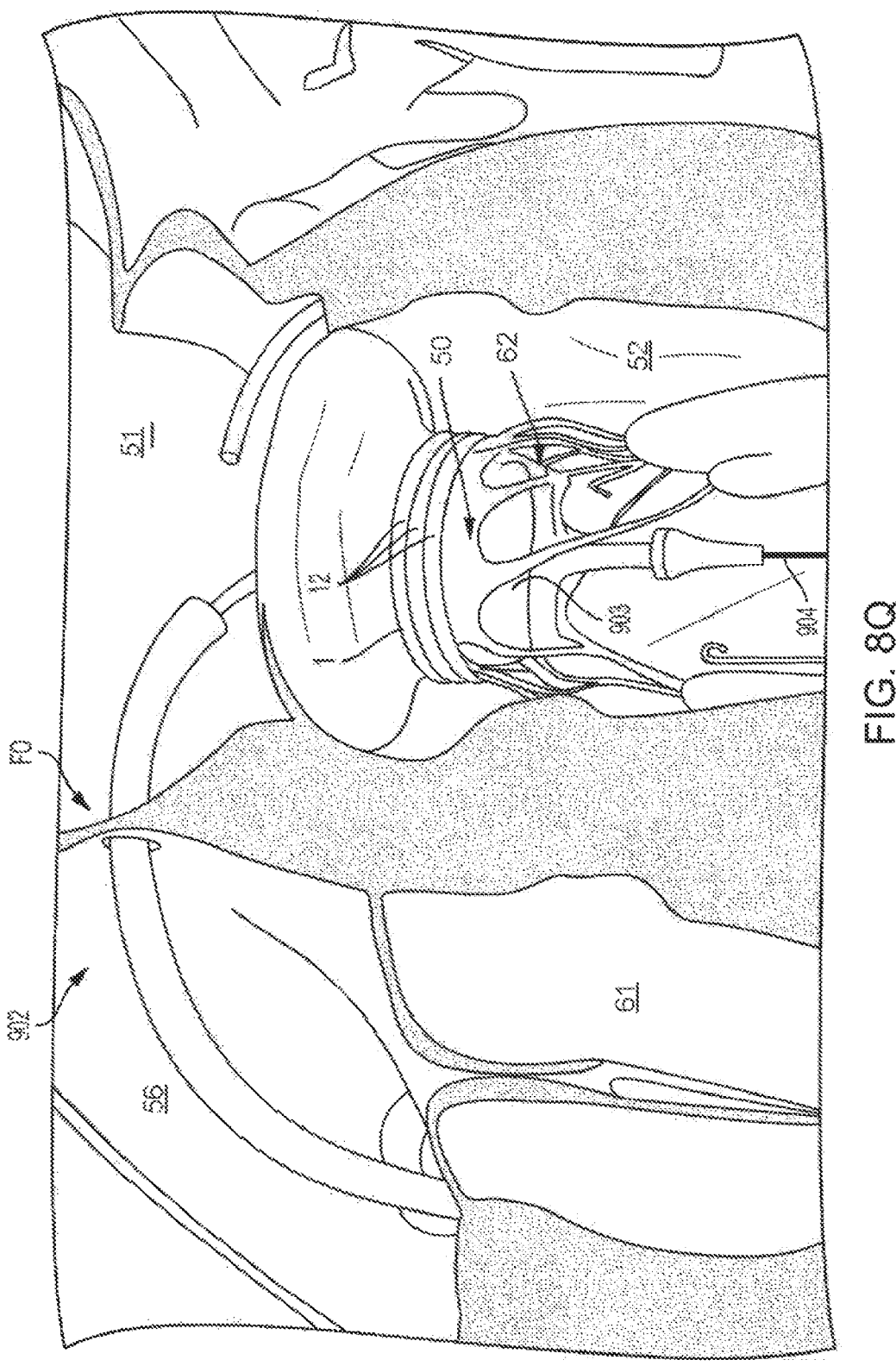
FIG. 8Q illustrates the heart valve of FIG. 8O being opened by inflation of a balloon to expand and attach the heart valve to the mitral valve of the patient.
Figure 8R:
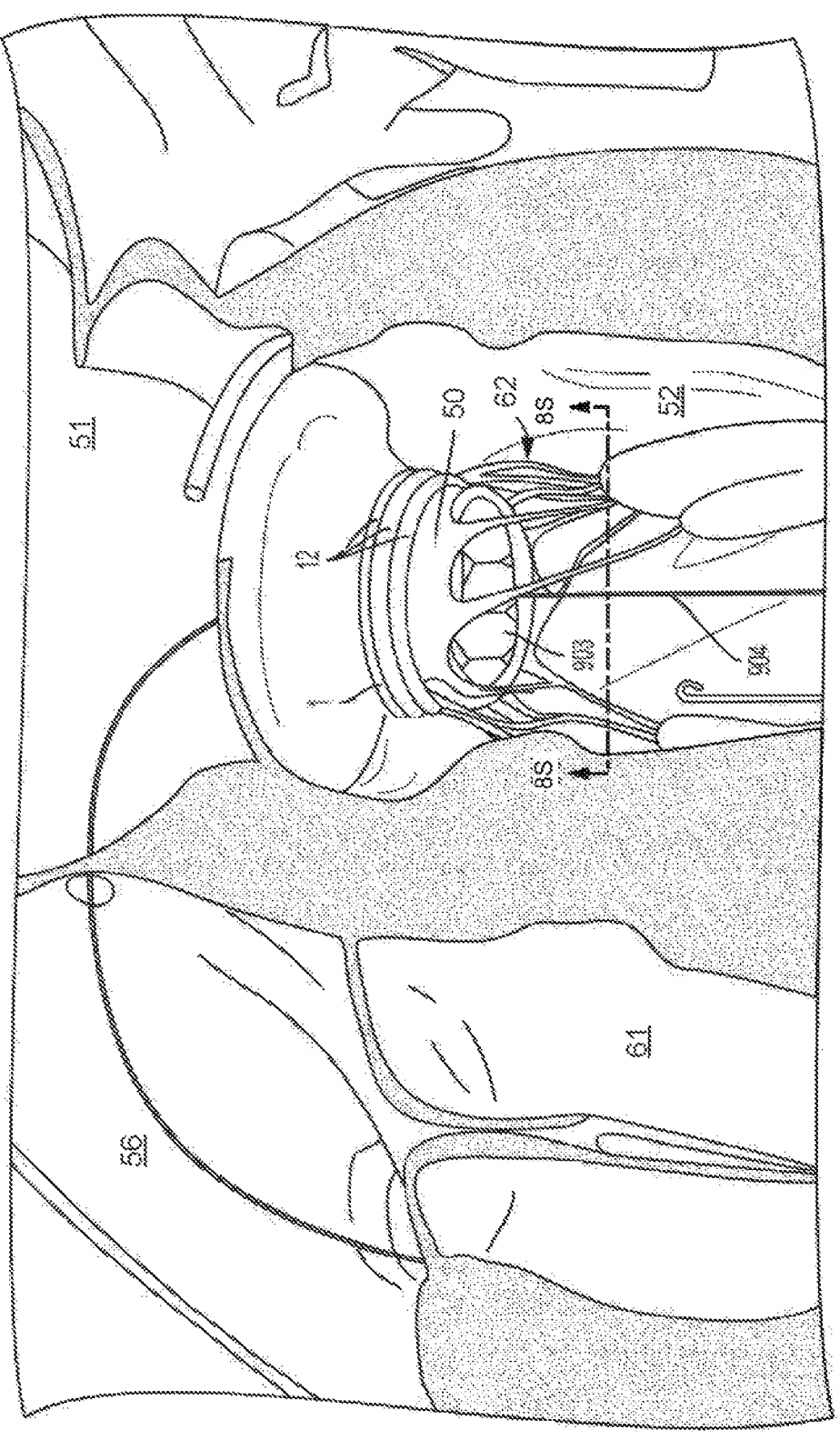
FIG. 8R illustrates the heart valve of FIG. 8O attached to the mitral valve of the patient's heart and secured by the anchoring device of FIG. 8I.
Figure 8S:
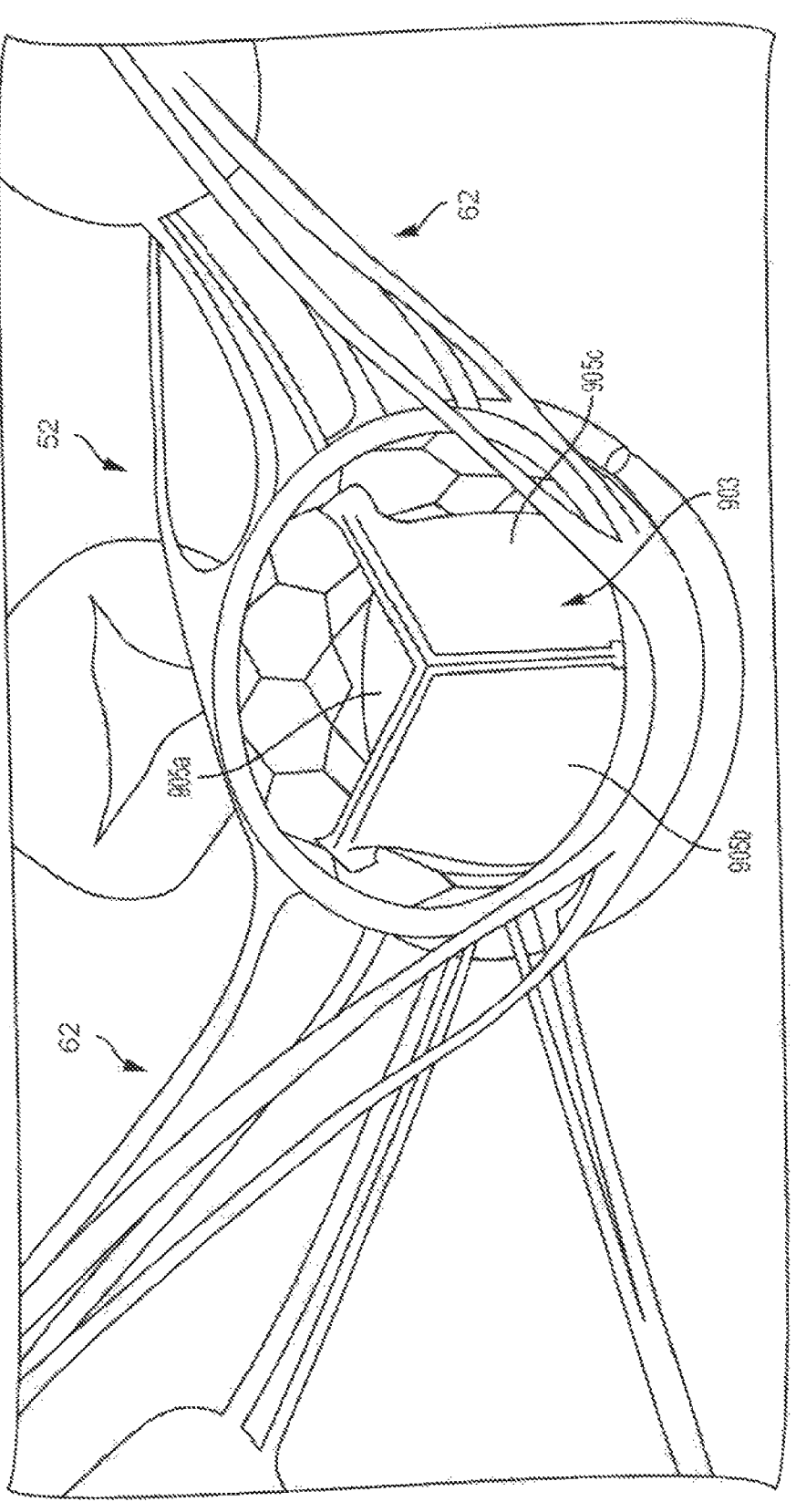
FIG. 8S is an upward view of the mitral valve from the left ventricle that illustrates the prosthetic heart valve of FIG. 8P attached to the mitral valve of the patient's heart from a view taken along the lines 8S-8S in FIG. 8R.

FIGS. 8A-8S, for example illustrate a method of utilizing the delivery catheter 100 to deliver an implant such as an anchoring device 1 to a native valve. The anchoring device 1 may comprise a docking device as disclosed herein. The flexible portion 102 of the delivery catheter 100 may have a spiral shape that is similar to the shape shown in FIG. 7C (although in an opposite direction of rotation in the embodiment shown).

The delivery catheter 100 may be delivered to a portion of a patient's body. The delivery catheter 100 may deliver and implant an implant in the form of an anchoring device (which can be the same as or similar to other anchoring devices described herein) at a native valve of a patient (e.g., at the native mitral valve 50 of a patient using a transseptal technique). FIG. 8A is a cutout view of the left atrium of a patient's heart that illustrates a sheath 20 (e.g., a guide sheath or transseptal sheath) of a sheath catheter passing through the interatrial septum, which can happen at the fossa ovalis (FO), and into the left atrium, and a delivery catheter 100 extending from the sheath 20. FIG. 8B illustrates the transseptal sheath 20 and the delivery catheter 100 in the position shown in FIG. 8A from a view looking down at the mitral valve 50 from the left atrium 51 (i.e., from a view taken along the line 8B-8B in FIG. 8A). Referring to FIG. 8A, the sheath 20 enters the left atrium such that the sheath is substantially parallel with the plane of the mitral valve 50. The sheath 20 and delivery catheter 100 can take any suitable form, such as, for example, any form described in the present application.

In some embodiments, the sheath 20 can be actuated or steerable as a steerable guide sheath so that the sheath 20 can be positioned or bent until it makes an angle (e.g., a 30-degree angle or an approximately 30-degree angle) with respect to the septum and/or FO wall. In some embodiments, the angle orientation (e.g., 30-degree angle orientation) can be adjusted or controlled by rotating or further actuating the sheath 20, and can be adjusted to better control the orientation at which the delivery catheter 100 enters the left atrium. In other embodiments, the deflection angle of the sheath 20 relative to the septum and/or FO can be either more or less than 30 degrees, depending on each situation, and in some applications, can even be oriented at or bent to be 90 degrees relative to the septum and/or FO. In certain embodiments, the deflection angle of the sheath can be moved between about 0 degrees and about 90 degrees, such as, for example, between about 5 degrees and about 80 degrees, such as between about 10 degrees and 70 degrees, such as between about 15 degrees and about 60 degrees, such as between about 20 degrees and about 50 degrees, such as between about 25 degrees and about 40 degrees, such as between about 27 degrees and about 33 degrees.

Referring to FIGS. 8C-8D, after the outer sheath or guide sheath 20 passes through the septum and/or FO and is placed in a desired position, the delivery catheter 100 exits and extends from the sheath 20. The delivery catheter 100 may be moved distally from the sheath 20 such that the delivery catheter 100 in such a configuration extends from the guide sheath 20 with a straightened shape. In embodiments, the flexible portion 102 of the delivery catheter 100 may initiate movement to a spiral shape, however, as shown in FIGS. 8C-8D, the delivery catheter 100 may extend in a straightened shape for some distance in the atrium. The delivery catheter 100 may be positioned in a desired location via the extension of the delivery catheter 100 from the guide sheath 20 and via deflection of the guide sheath 20 to a desired amount. The guide sheath 20 as shown in FIGS. 8C-8D, for example, may be deflected in a ventricular direction to angle the delivery catheter 100 in such a direction. The deflection of the guide sheath 20 may be against the passively flexible portion 152 of the delivery catheter as shown in FIG. 6D in embodiments, to deflect the distal portion of the delivery catheter.

The tether of the delivery catheter 100 may have a longitudinal force applied to the tether to form the flexible portion 102 into a spiral shape (as shown in FIG. 7C for example) from a straightened shape. FIGS. 8E and 8F, for example, illustrate the flexible portion 102 curved into a spiral shape with the atrium. The tether may comprise a pull tether that is retracted proximally. The flexible portion 102 curves in a counter-clockwise direction to create a circular/curved path, in which the anchoring device can also coil in a counter-clockwise direction. In alternative embodiments, the distal tip 114 is moved such that the distal tip 114 curves in the clockwise direction to create a circular/curved path (in these embodiments the anchoring device can also coil in a clockwise direction).

As shown in FIG. 8E, the delivery catheter 100 may spiral downward until the circular/curved planar portion of the distal tip 114 nears the plane of the mitral valve 50, which is generally about 30 to 40 mm below the FO wall. In some situations, however, the plane of the mitral valve may be less than 30 mm below the FO or more than 30 mm below the FO. In certain embodiments, the delivery catheter 100 is configured to extend 60 mm or less from the outer sheath, such as, for example, 50 mm or less, such as 45 mm or less, such as 40 mm or less, such as 35 mm or less, such as 30 mm or less, such as 25 mm or less, such as 20 mm or less. In some embodiments, the maximum extension of the delivery catheter 100 from the exterior sheath is between about 20 mm and about 60 mm, such as, for example, between about 25 mm and about 50 mm, such as between 30 mm and about 40 mm.

The lower curved portion of the spiral shape may be lowered to or near the level of the annulus, the lower curved portion can be parallel or nearly parallel (e.g., planar or nearly planar) with a plane of the annulus, or the lower curved can be slightly upwardly angled relative to the plane of the annulus.

Further, a torqueing or rotating of the guide sheath 20 may be utilized to get the angles right if the actuations of the curved portions does not fully position the distal region of the catheter as desired.

FIG. 8G illustrates the delivery catheter 100 deploying an exemplary embodiment of an anchoring device 1 through the commissure A3P3 and around the chordae tendineae 62 and native leaflets in the left ventricle 52 of the patient's heart. The anchoring device 1 or a lower end or encircling coil/turn of the anchoring device with a larger diameter or radius of curvature exits the distal opening of the delivery catheter 100 and begins to take its shapeset or shape memory form in the direction of the delivery catheter 100. The anchoring device 1 may comprise a docking coil that is passed through the inner lumen of the flexible portion of the catheter 100 to deploy to the native heart valve while the flexible portion is in the spiral shape.

For the anchoring device 1 to move through the commissure A3P3 of the mitral valve 50, the delivery catheter 100 is positioned such that the distal tip 114 of the delivery catheter 100 is directed toward and/or into the commissure A3P3. After the anchoring device 1 exits the delivery catheter 100, the anchoring device 1 begins to curve to take its shapeset or shape memory form. The anchoring device 1 may be deployed, as illustrated by FIG. 8G.

Referring to FIG. 8H, with the distal tip 114 substantially planar with the mitral valve annulus, the anchoring device 1 can be further deployed from the delivery catheter 100, such that the anchoring device wraps around the chordae tendineae 62 in a position that is substantially parallel to the plane of the mitral valve 50. This prevents the anchoring device from curving in an upward direction and engaging the underside of the mitral valve annulus and/or the top wall of the left ventricle.

Referring to FIG. 8I, the anchoring device 1 is disposed around the chordae tendineae 62 to loosely position the anchoring device on the ventricular side of the mitral valve for holding a heart valve. In the illustrated embodiment, the anchoring device 1 is disposed in the left ventricle 52 such that three functional coils 12 of the anchoring device are wrapped closely around the chordae tendineae and/or native leaflets. The lower end turn/coil or encircling turn/coil can be seen extending outwardly somewhat because of its larger radius of curvature. In some embodiments, the anchoring device 1 can include less than three coils 12 or more than three coils 12 that are disposed around the chordae tendineae and/or leaflets.

FIG. 8J illustrates the delivery catheter 100 in the left atrium 51 in a position after the coils 12 of the anchoring device are disposed around the chordae tendineae 62 and native leaflets (as shown in FIG. 8I). In this position, the distal tip 114 of the delivery catheter 100 is substantially parallel with the plane of the mitral valve 50 and is located at or near (e.g., extending slightly into or through, such as 1-5 mm or less) the commissure A3P3 of the mitral valve 50.

Referring to FIG. 8K, after the delivery catheter 100 and the anchoring device 1 are positioned as shown in FIGS. 8G-8I, the delivery catheter is translated or retracted axially along the anchoring device in the direction X and into the outer sheath 20. Translation or retracting of the delivery catheter can cause the portions of the anchoring device positioned one the atrial side of the native valve (e.g., in the atrium) to be unsheathed and released from the delivery catheter. For example, this can unsheath and release any upper portion of any functional coil and/or upper coil positioned on the atrial side of the native valve (if any). In one exemplary embodiment, the anchoring device 1 does not move or does not substantially move as the delivery catheter is translated, e.g., a pusher can be used to hold the anchoring device in place and/or inhibit or prevent retraction of the anchoring device when the delivery catheter is retracted.

Referring to FIG. 8L, in the illustrated example, translation or retraction of the delivery catheter can also unsheath/release any upper end coil/turn (e.g., a larger diameter stabilization coil/turn) of the anchoring device 1 from the delivery catheter. As a result of the unsheathing/releasing, the atrial side of the anchoring device or upper coil (e.g., stabilization coil with a larger diameter or radius of curvature) extends out of the delivery catheter 100 and begins to assume its preset or relaxed shape-set/shape-memory shape. The anchoring device can also include an upward extending portion or connecting portion that extends upward from a bend Z and can extend and/or bridge between an upper end stabilization coil/turn and other coil/turns of the anchoring device (e.g., functional coils/turns). In some embodiments, the anchoring device can have only one upper coil on the atrial side of the native valve. In some embodiments, the anchoring device can include more than one upper coil on the atrial side of the native valve.

Referring to FIG. 8M, the delivery catheter 100 continues to translate back into the outer sheath or guide sheath 20, which causes the upper portion of the anchoring device 1 to be released from inside the delivery catheter. The anchoring device is connected closely to the pusher 950 by an attachment means, such as suture/line 901 (other attachment or connection means can also be used as desired). The upper end coil/turn or stabilization coil/turn is shown as being disposed along the atrial wall to temporarily and/or loosely hold the position or height of the anchoring device 1 relative to the mitral valve 50.

Referring to FIG. 8N, the anchoring device 1 is fully removed from a lumen of the delivery catheter 100, and slack is shown in a suture/line 901 that is removably attached to the anchoring device 1, e.g., suture/line 901 can loop through an eyelet at the end of the anchoring device. To remove the anchoring device 1 from the delivery catheter 100, the suture 901 is removed from the anchoring device. However, before the suture 901 is removed, the position of the anchoring device 1 can be checked. If the position of the anchoring device 1 is incorrect, the anchoring device can be pulled back into the delivery catheter by the pusher 950 (e.g., a pusher rod, pusher wire, pusher tube, etc.) and redeployed.

Referring to FIG. 8O, after the delivery catheter 100 and the outer sheath 20 are detached from the anchoring device 1, a heart valve delivery device/catheter 902 can be used to deliver a heart valve 903 to the mitral valve 50. The heart valve delivery device 902 may utilize one or more of the components of the delivery catheter 100 and/or outer or guide sheath 20 or the delivery device 902 may be independent of the delivery catheter 100 and outer or guide sheath. In the illustrated embodiment, the heart valve delivery device 902 enters the left atrium 51 using a transseptal approach. In embodiments, the heart valve delivery catheter 902 may be passed through the outer sheath 20. The heart valve delivery catheter 902 may deploy the prosthetic heart valve to dock with an anchoring device 1 in the form of a docking coil.

Referring to FIG. 8P, the heart valve delivery device/catheter 902 is moved through the mitral valve 50 such that heart valve 903 is placed between the leaflets of the mitral valve and the anchoring device 1. The heart valve 903 can be guided along a guide wire 904 to the deployment position.

Referring to FIG. 8Q, after the heart valve 903 is placed in the desired position, an optional balloon is expanded to expand the heart valve 903 to its expanded, deployed size. That is, the optional balloon is inflated such that the heart valve 903 engages the leaflets of the mitral valve 50 and forces the ventricular turns outward to an increased size to secure the leaflets between the heart valve 903 and the anchoring device. The outward force of the heart valve 903 and the inward force of the coil 1 can pinch the native tissue and retain the heart valve 903 and the coil to the leaflets. In some embodiments, a self-expanding heart valve can be retained in a radially compressed state within a sheath of the heart valve delivery device 902, and the heart valve can be deployed from the sheath, which causes the heart valve to expand to its expanded state. In some embodiments, a mechanically expandable heart valve is used or a partially mechanically expandable heart valve is used (e.g., a valve that may expand by a combination of self-expansion and mechanical expansion).

Referring to FIG. 8R, after the heart valve 903 is moved to its expanded state, the heart valve delivery device 902 and the wire 904 (still shown in FIG. 8R) are removed from the patient's heart. Further, the guide sheath 20 may be removed from the patient's heart as well. The heart valve 903 is in a functional state and replaces the function of the mitral valve 50 of the patient's heart.

FIG. 8S shows the heart valve 903 from an upward view in the left ventricle 52 along the lines U-U in FIG. 8R. In FIG. 8S, the heart valve 903 is in the expanded and functional state. In the illustrated embodiment, the heart valve 903 includes three valve members 905a-c (e.g., leaflets) that are configured to move between an open position and a closed position. In alternative embodiments, the heart valve 903 can have more than three valve members or less than three valve members that are configured to move between an open position and a closed position, such as, for example, two or more valve members, three or more valve members, four or more valve members, etc. In the illustrated embodiment, the valve members 905a-c are shown in the closed position, which is the position the valve members are in during the systolic phase to prevent blood from moving from the left ventricle and into the left atrium. During the diastolic phase, the valve members 905a-c move to an open position, which allows blood to enter the left ventricle from the left atrium.

While the embodiment illustrated in FIGS. 8A-8S show the delivery catheter 100 delivering an anchoring device 1 through the commissure A3P3, it should be understood that the delivery catheter 100 can take a configuration and be positioned to deliver the anchoring device 1 through the commissure A1P1, such that the anchoring device 1 can be wrapped around the chordae tendineae in the left ventricle of the patient's heart. In addition, while the illustrated embodiments show the delivery catheter 100 delivering an anchoring member 1 to the mitral valve and the heart valve delivery device 902 delivering a heart valve 903 to the mitral valve 50, it should be understood that the anchoring device 1 and the heart valve 903 can be used mutatis mutandis to repair the tricuspid valve, the aortic valve, or the pulmonary valve.

Figure 9A:
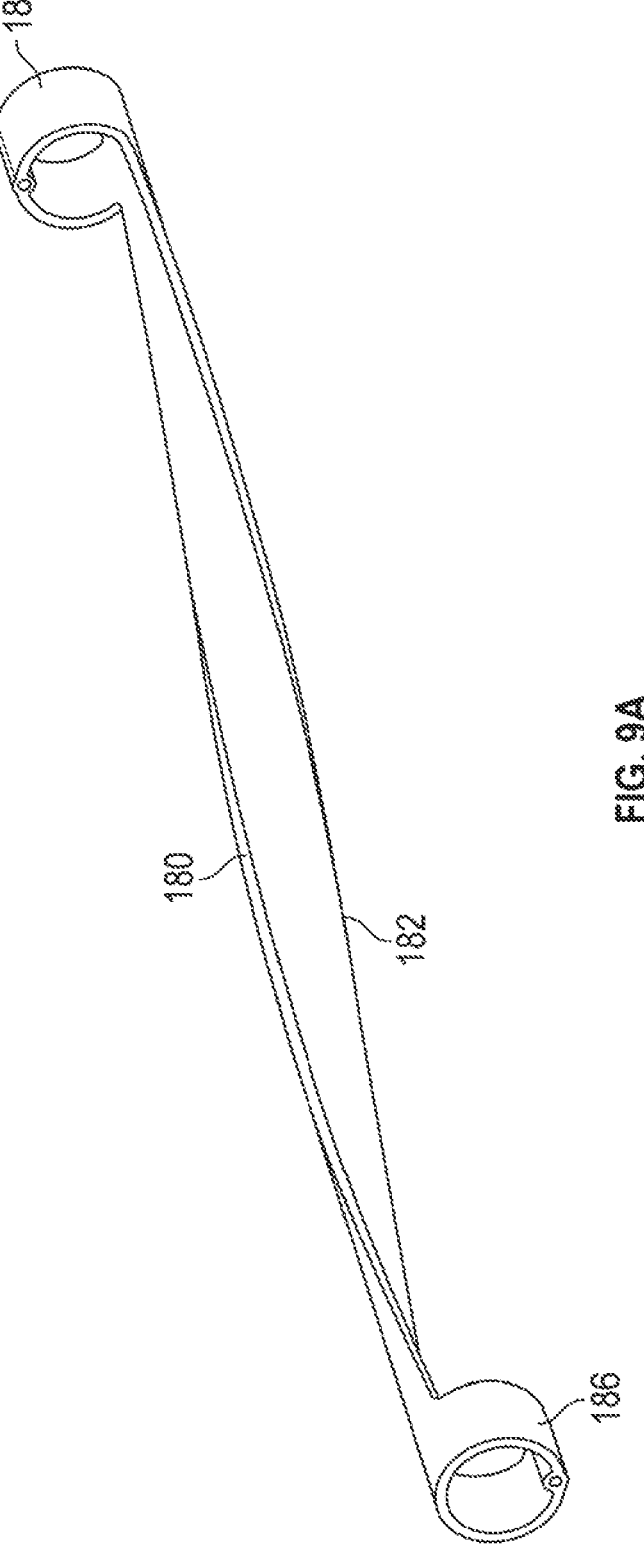
FIG. 9A shows a perspective view of a spine according to an embodiment of the present disclosure.

The configuration of the spine, and corresponding configuration of the tether channel and tether may be varied in embodiments. FIG. 9A, for example, illustrates an embodiment of a spine 180 having a half rotation (similar to the embodiment shown in FIGS. 7A-7C). The elongate strip 182 may rotate at a half rotation between a proximal ring 184 and a distal ring 186. The rotation may be counter-clockwise as shown in FIG. 9A, or in embodiments may be clockwise as desired.

Figures 9B, 9C:
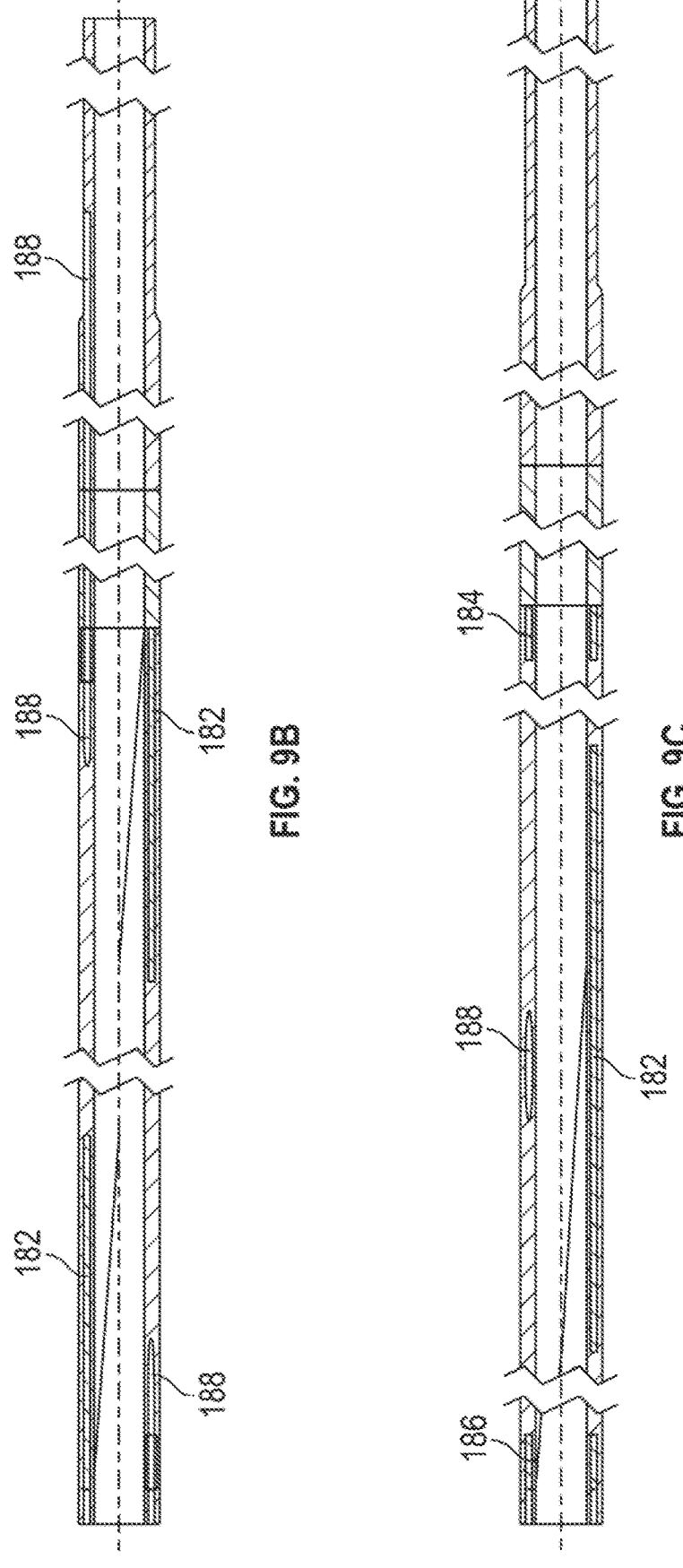
FIG. 9B shows a cross sectional view of an elongate shaft of a delivery catheter along a mid line.
FIG. 9C shows a cross sectional view of an elongate shaft of a delivery catheter along a view rotated 90 degrees from the view shown in FIG. 9B.

FIG. 9B illustrates a cross sectional view of an elongate shaft including the spine 180 along a mid line of the elongate shaft. FIG. 9C illustrates a cross sectional view of the elongate shaft rotated 90 degrees from the position shown in FIG. 9B. The tether channel 188 is shown extending in a spiral opposite the spiral of the elongate strip 182.

Figure 10A:
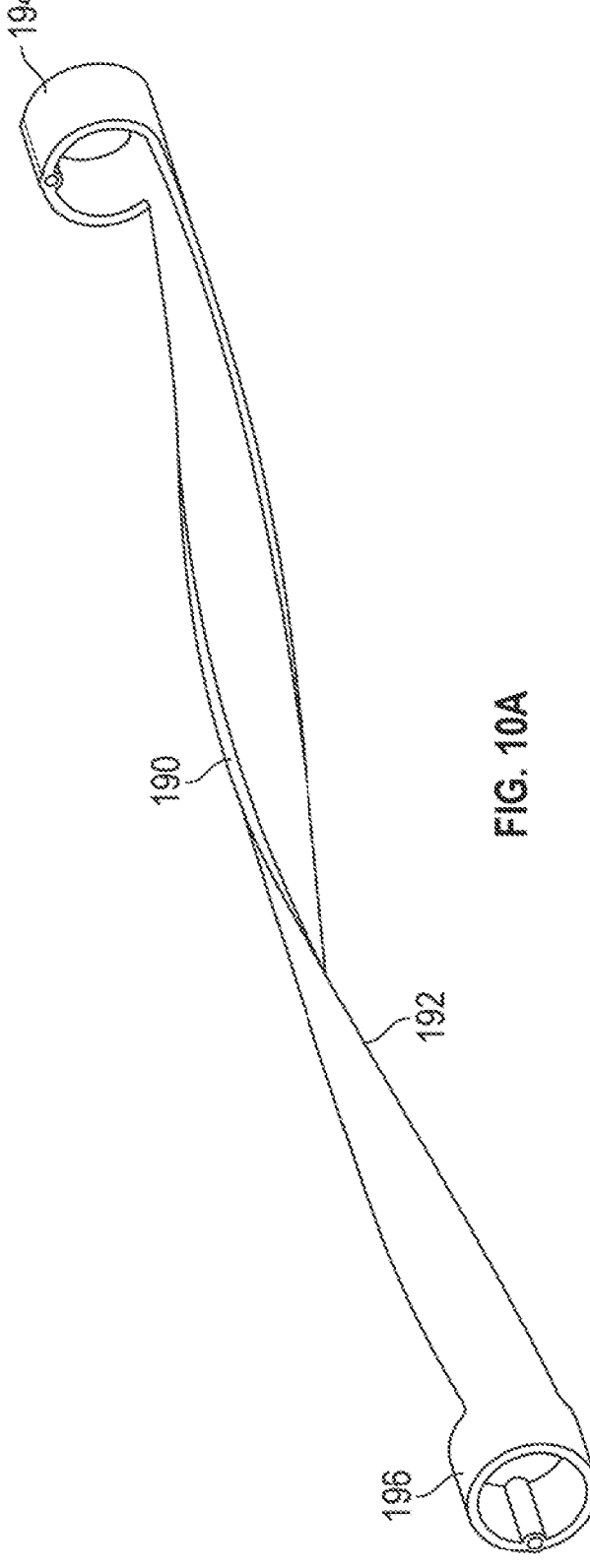
FIG. 10A shows a perspective view of a spine according to an embodiment of the present disclosure.

FIG. 10A illustrates an embodiment of a spine 190 having a three-quarters rotation. The elongate strip 192 may rotate at a three-quarters rotation between a proximal ring 194 and a distal ring 196. The rotation may be counter-clockwise as shown in FIG. 10A, or in embodiments may be clockwise as desired.

Figures 10B, 10C:
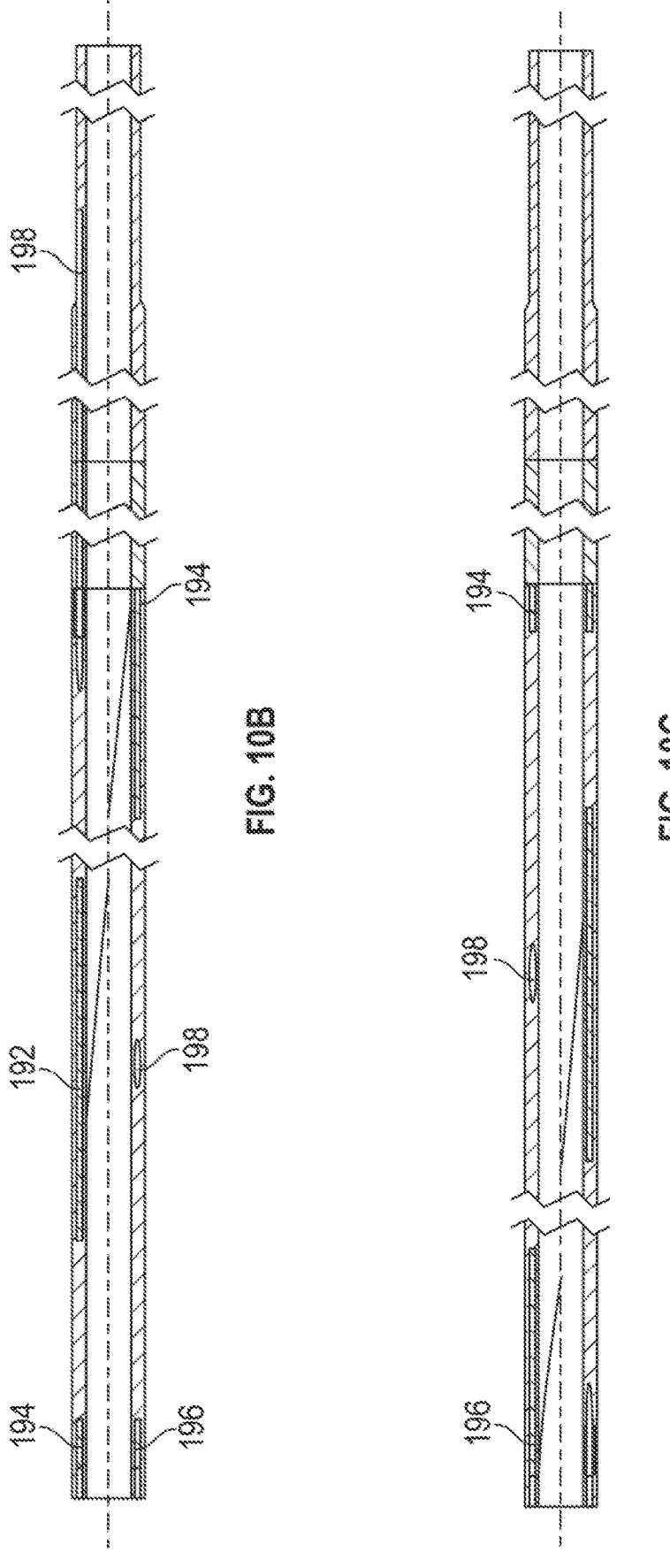
FIG. 10B shows a cross sectional view of an elongate shaft of a delivery catheter along a mid line.
FIG. 10C shows a cross sectional view of an elongate shaft of a delivery catheter along a view rotated 90 degrees from the view shown in FIG. 10B.

FIG. 10B illustrates a cross sectional view of an elongate shaft including the spine 190 along a mid line of the elongate shaft. FIG. 10C illustrates a cross sectional view of the elongate shaft rotated 90 degrees from the position shown in FIG. 10B. The tether channel 198 is shown extending in a spiral opposite the spiral of the elongate strip 192.

FIG. 11A illustrates an embodiment of a spine 200 having a three-quarters rotation. The elongate strip 202 may rotate at a three-quarters rotation between a proximal ring 204 and a distal ring 206. The rotation may be counter-clockwise as shown in FIG. 11A, or in embodiments may be clockwise as desired. The elongate strip 202 of the spine 200 may include a cut-out portion 203 that may extend longitudinally along the elongate strip 202. In embodiments, the cut-out portion may extend between two elongate portions of the elongate strip 202, or other configurations may result in embodiments (e.g., three elongate portions resulting, or other configurations of elongate strips 202 resulting).

FIG. 11B illustrates a cross sectional view of an elongate shaft including the spine 200 along a mid line of the elongate shaft. FIG. 11C illustrates a cross sectional view of the elongate shaft rotated 90 degrees from the position shown in FIG. 11B. The tether channel 208 is shown extending in a spiral opposite the spiral of the elongate strip 202.

The embodiments of spines disclosed herein, as such, may have an amount of rotation as desired. The rotation, for example, in embodiments, may be at least a half rotation by the elongate strip about the flexible portion, at least a three-quarters rotation, or may comprise at least a full rotation, among other amounts of rotation.

Figure 12A:
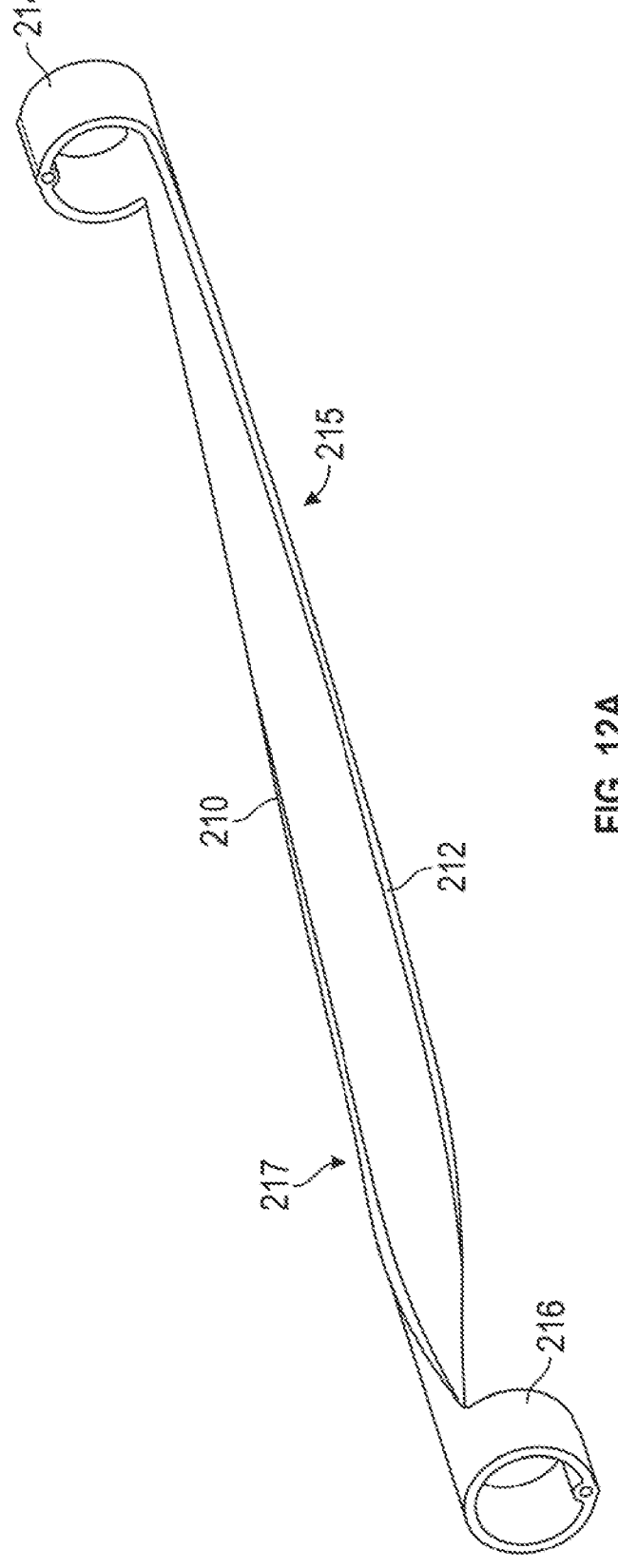
FIG. 12A shows a perspective view of a spine according to an embodiment of the present disclosure.

FIG. 12A illustrates an embodiment of a spine 210 having a half rotation. The rotation may be counter-clockwise as shown in FIG. 12A, or in embodiments may be clockwise as desired. The elongate strip 212 may rotate at a half rotation between a proximal ring 214 and a distal ring 216. The pitch of rotation of the elongate strip 212 may vary along the length of the strip 212 and the flexible portion. For example, a proximal portion 215 of the elongate strip 212 may have a lesser pitch than a distal portion 217 of the elongate strip 212. In embodiments, the proximal portion 215 may have a greater pitch than the distal portion 217, or other variations may be utilized (e.g., a mid section having a different pitch than adjacent portions). The pitch of the elongate strip 212 may be set to allow the spine 210 to flex into a spiral having a desired shape. In embodiments, the pitch of the spine, or variation in the pitch of the spine along its length may be set as desired. In embodiments, a width, or thickness, or other geometric characteristics of the spine may be set to provide a desired shape of spiral.

Figures 12B, 12C:
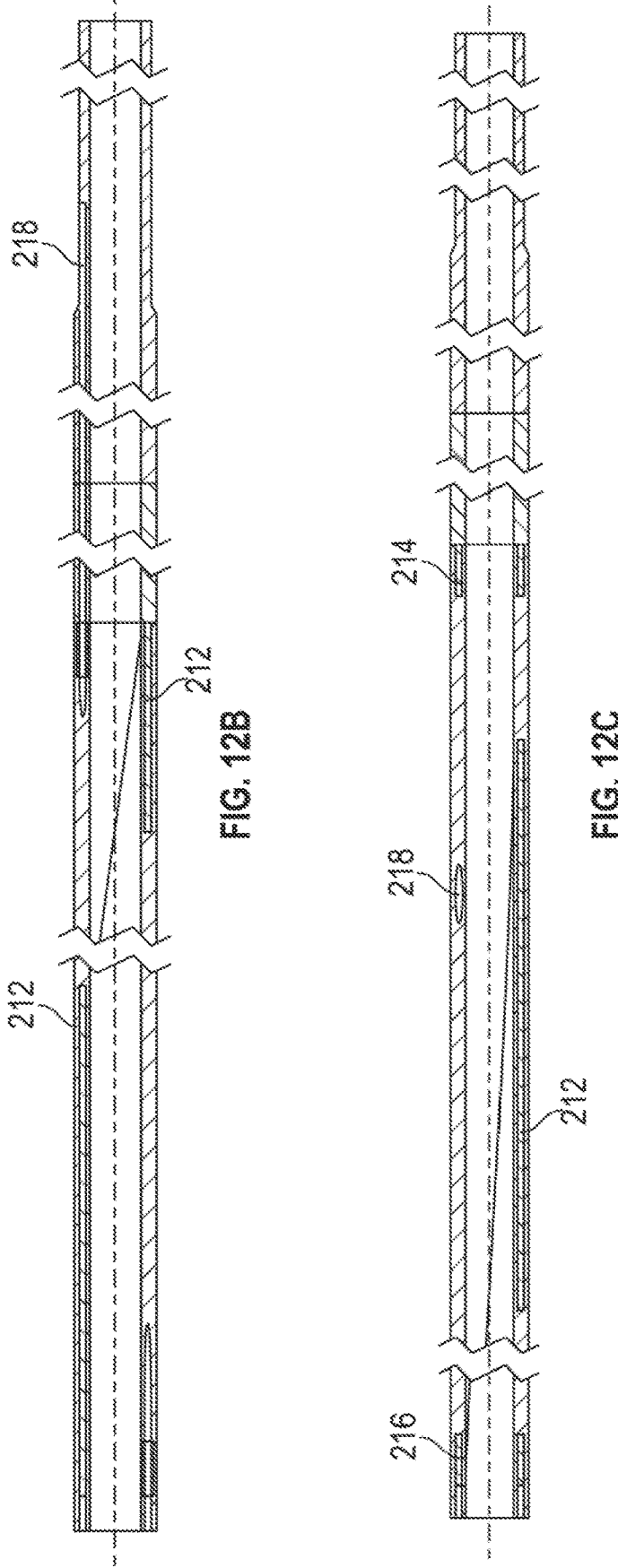
FIG. 12B shows a cross sectional view of an elongate shaft of a delivery catheter along a mid line.
FIG. 12C shows a cross sectional view of an elongate shaft of a delivery catheter along a view rotated 90 degrees from the view shown in FIG. 12B.

FIG. 12B illustrates a cross sectional view of an elongate shaft including the spine 210 along a mid line of the elongate shaft. FIG. 12C illustrates a cross sectional view of the elongate shaft rotated 90 degrees from the position shown in FIG. 12B. The tether channel 218 is shown extending in a spiral opposite the spiral of the elongate strip 212.

Various other configurations of spines and flexible portions of elongate shafts may be utilized in embodiments. Combinations of features across embodiments may be provided (e.g., varying pitch of elongate strips, cut-out portions, and amounts of rotation, among other features).

In embodiments, the spine may be made of a variety of materials including a metal, or a high durometer polymer, among other forms of materials. The spine may be made of PEBAX in embodiments. In certain embodiments, the spine may be made of a shape memory material such as nitinol or another form of shape memory material. A shape memory material may aid the spine to move to a spiral shape upon deployment in embodiments.

A lubricious coating may be applied to the inner lumen of the elongate shaft, along with the tether channel. The outer surface of the elongate shaft may further include a lubricious coating in embodiments.

In embodiments, compression coils may be added to the tether to localize the flex of the elongate shaft and prevent flexing when the elongate shaft experiences tortuosity.

In embodiments, tubular braided material may be added to the body of the elongate shaft to provide a variety of benefits, including improved tensile properties, resistance to kinking and distortion, limiting elongation, providing torque transmission capabilities, increasing column strength, and/or providing radiopacity. For example, in FIG. 6C, a braid layer may be positioned between the tether channel and an outer or inner jacket that covers the tether channel and the spine.

In embodiments, radiopaque markers may be included in the catheter to provide localized radiopacity in the elongate shaft.

In embodiments, the body of the elongate shaft may comprise a multi-layered structure with tie layers between the layers.

In embodiments, additional flex points may be provided for the elongate shaft, including flex points proximal or distal of the spiral spine. Such flex points may be controlled with additional tethers or other forms of deflection mechanism.

Figure 13A:
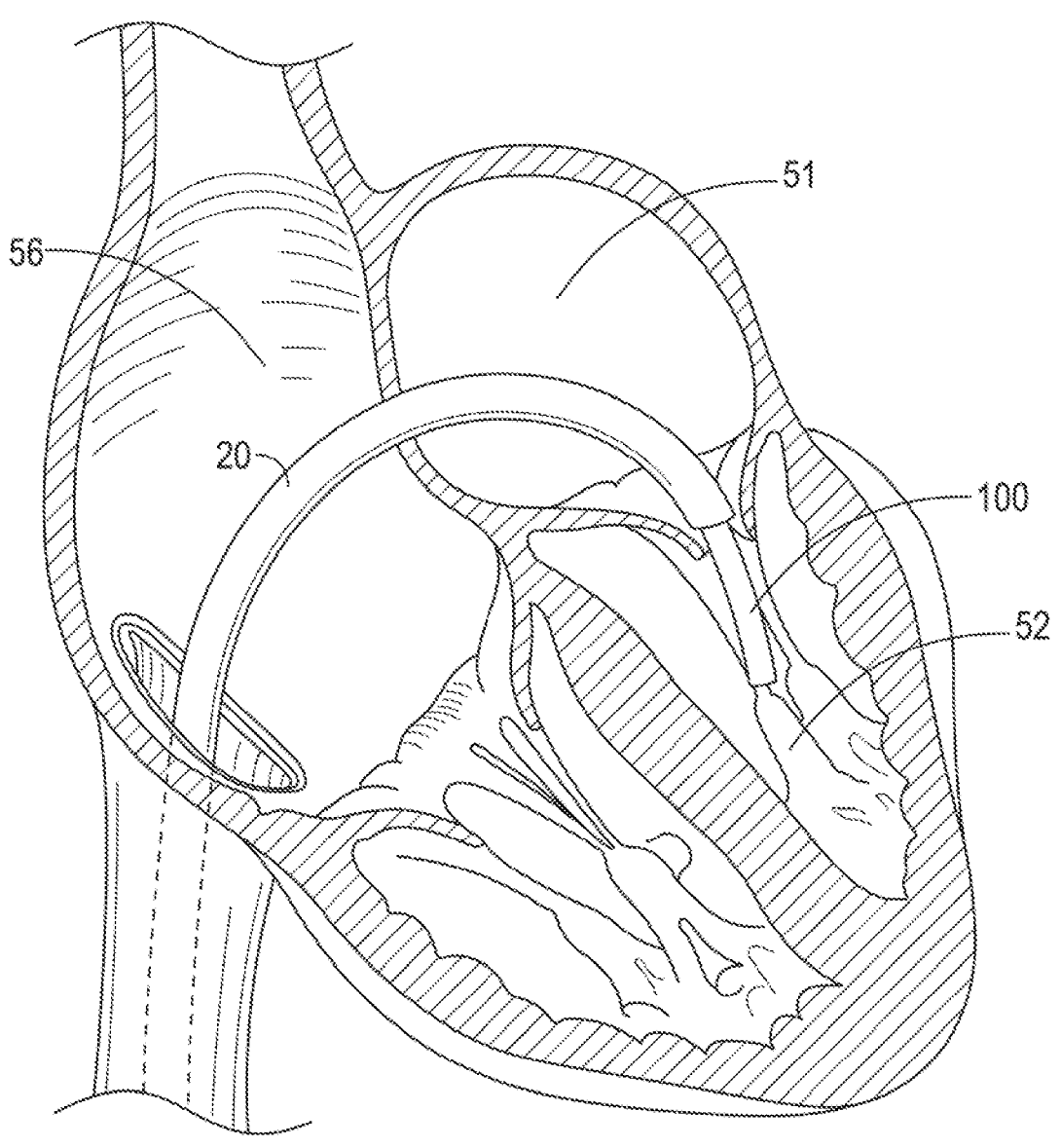
FIG. 13A shows a partial perspective view of a delivery catheter entering a ventricle according to an embodiment herein.

In embodiments, the delivery catheter may be passed into the ventricle of the patient's heart to deploy an implant. The flexible portion of the delivery catheter may be moved to the spiral shape within a ventricle of the patient's heart. FIG. 13A, for example, illustrates the delivery catheter 100 passing through a valve annulus into a ventricle. The delivery device shown includes a sheath catheter including an outer guide sheath 20. The delivery device includes a delivery catheter 100 that can be advanced through and out of a distal end of the guide sheath 20. In the embodiment shown, the guide sheath 20 can first be steered through an opening that is formed in the interatrial septum (e.g., at the fossa ovalis), and into the left atrium. The guide sheath 20 can then be manipulated to curve or bend downwards towards the native mitral valve annulus, so that the distal opening of the guide sheath 20 points substantially coaxially with a central axis of the mitral annulus. A vertical position of the guide sheath 20 can be such that the distal opening of the guide sheath 20 is substantially aligned with the native mitral annulus, or can be positioned in the left atrium slightly above the native mitral annulus, or, in some embodiments can extend through the native mitral annulus and into the left ventricle.

Once the guide sheath 20 is positioned substantially as shown in FIG. 13A, the delivery catheter 100 may then be advanced out of the distal opening of the guide sheath 20. In this embodiment, the distal end of the guide sheath 20 is positioned at or slightly above the native mitral annulus, so that the delivery catheter 100 can first be advanced into the left atrium, just above the native mitral annulus. The delivery catheter 100 can initially be advanced out of the distal opening of the guide sheath 20 in an unactuated, substantially straightened configuration, and can thereafter be actuated into the spiral configuration shown in FIG. 13C after advancement out of the guide sheath 20.

Figure 13B:
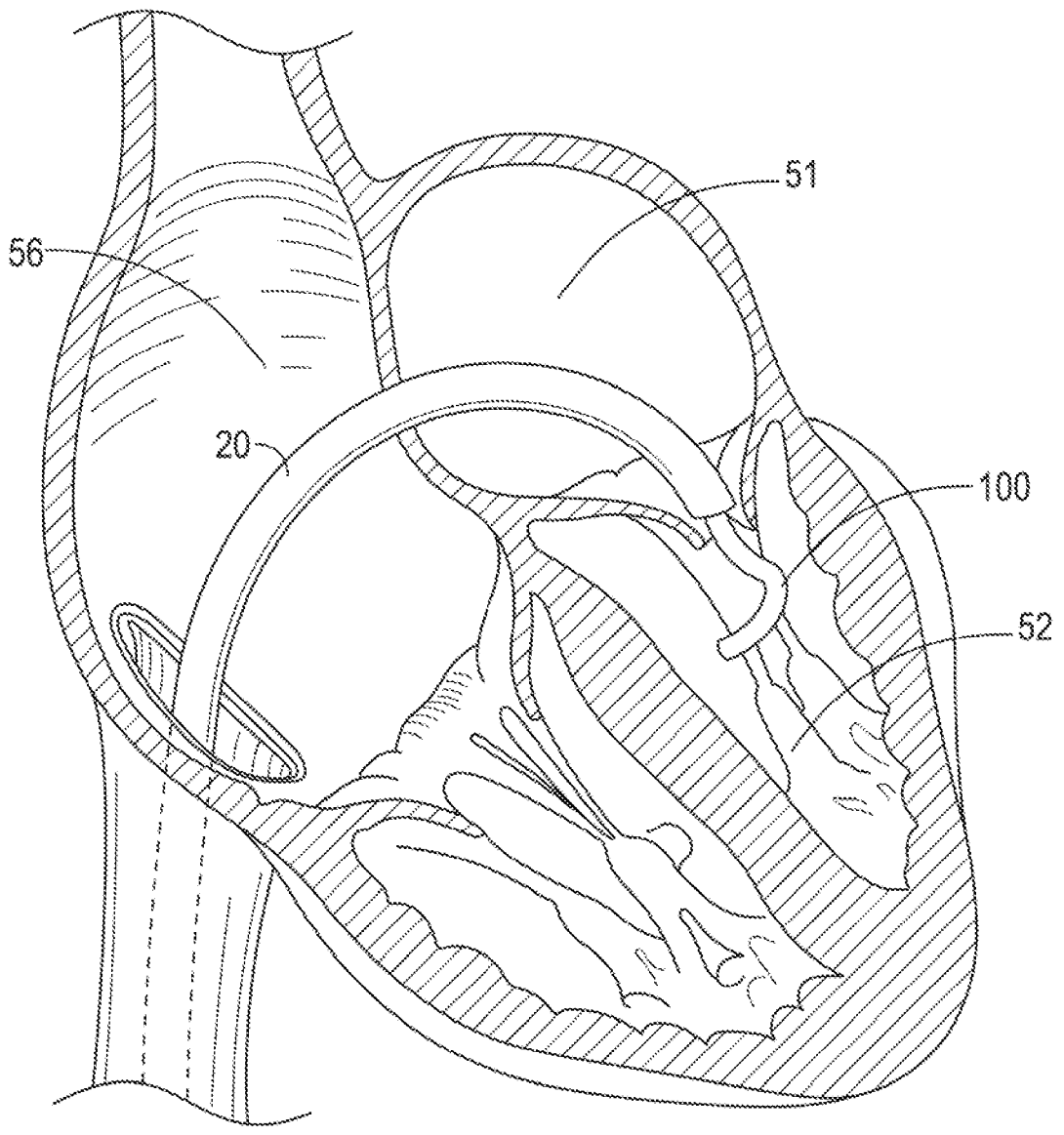
FIG. 13B shows the delivery catheter shown in FIG. 13A flexed from the position shown in FIG. 13A.
Figure 13C:
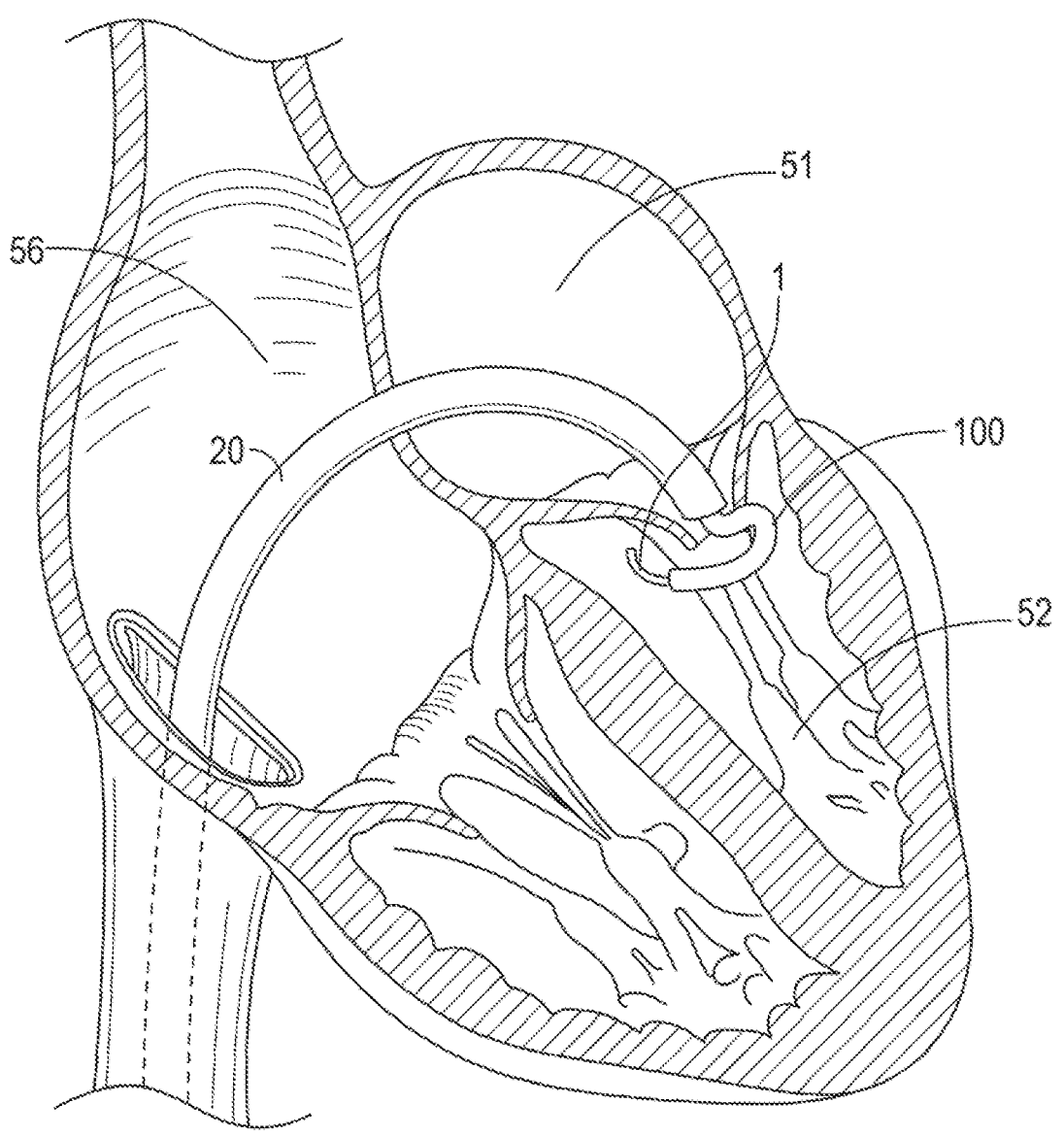
FIG. 13C shows the delivery catheter shown in FIG. 13B flexed from the position shown in FIG. 13B.

FIG. 13B, for example, illustrates the delivery catheter 100 being flexed into a spiral shape. The delivery catheter 100 may extend around the leaflets of the native valve in such a configuration. FIG. 13C illustrates the delivery catheter 100 having a spiral shape around the leaflets of the native valve. The anchoring device 1 may be deployed in such a configuration. In some embodiments, the delivery catheter 100 can be actuated to any other suitable configuration, such as, for example, any configuration described in the present application.

In embodiments herein, once the guide sheath 20 is arranged or positioned as desired (e.g., as shown or described elsewhere herein, for example, crossing the septum in a mitral procedure), a portion of a delivery catheter 100 is advanced out of the distal opening of the guide sheath 20. The portions of the delivery catheter 100 that extend out of the guide sheath 20 can be positioned in the left atrium before the delivery catheter is adjusted to its actuated configuration or final actuated configuration. In some cases, part of the delivery catheter can also extend (e.g., as in FIG. 13A or with just the tip extending slightly, such as 1-5 mm or less) into the left ventricle through the native mitral valve before the delivery catheter is adjusted to its actuated configuration or final actuated configuration.

In some circumstances, formation of the delivery catheter 100 into a spiral shape may not alone be enough to properly position the distal tip at or near the commissure in a desired position for delivery, and torqueing or rotating the delivery device or a portion thereof (e.g., rotating the delivery catheter and/or guide sheath) can be used to angle the delivery catheter and a tip of the delivery catheter as desired. For example, after the distal flexible portion of the delivery catheter 100 is fully actuated into a spiral as desired (e.g., as described above), the assembly can be torqued and rotated to cause the tip of the delivery catheter 100 to be angled or aligned at or into a commissure of the native valve, for example, at commissure A3P3 of the mitral valve. The delivery catheter 100 can then be further torqued and rotated so that the distal tip of the delivery catheter 100 passes through the commissure and into the left ventricle. Optionally, further rotation and/or actuation of the delivery catheter 100 can then facilitate circumferential advancement of the distal tip of the delivery catheter 100 in the left ventricle, to be looped or positioned around an outside of the mitral anatomy, for example, chordae tendineae, papillary muscles, and/or other features in the left ventricle.

Referring to FIGS. 13A-C, if a user elects to move the distal region of the catheter into a ventricle (e.g., left or right ventricle), movement of the delivery catheter 100 around the anatomy in the ventricle can serve to gather or capture the corralled anatomy within the spiral shape. In some embodiments, after the distal flexible portion of the delivery catheter 100 is moved to a desired position around the chordae and other features in the ventricle, the spiral shape may be tightened in order to cinch and gather the chordae and other native anatomy passing through the spiral even further towards the center of the native annulus. Such radial cinching or gathering of the native anatomy in the ventricle can help facilitate an even more robust delivery of the anchoring device 1 later, for example, by making it easier for the anchoring device 1 to be advanced around the gathered chordae and other features.

After the delivery catheter 100 has been satisfactorily positioned around the chordae and other desired anatomy in the left ventricle, the anchoring device 1 can be advanced out of the distal opening of the delivery catheter 100. The curved shape of the spiral can facilitate smoother and easier extrusion of the anchoring device 1 from the delivery catheter 100, since the curvature can be formed to be substantially similar to the final curvature of the anchoring device 1. Once the ventricular portion of the anchoring device 1 has been advanced to a desired position in the left ventricle, the atrial portion of the anchoring device 1 can be released from the delivery catheter 100 in a similar manner as one of the various ways discussed above, for example, by backwards movement of the delivery catheter 100. Such movement can also help retract the delivery catheter 100 itself out of the left ventricle and back into the left atrium. Then, after the anchoring device 1 has been fully delivered and moved to a desired position, the delivery catheter 100 can be straightened and retracted back through the guide sheath 20. Thereafter, a prosthesis (e.g., a THV or other prosthetic valve) can be advanced to and expanded in the anchoring device 1, similarly as previously discussed.

Optionally, the anchoring or docking device can also include a low-friction sleeve, e.g., a PTFE sleeve, that fits around all or a portion (e.g., the leading and/or functional turns) of the anchoring or docking device. For example, the low-friction sleeve can include a lumen in which the anchoring device (or a portion thereof) fits. The low-friction sleeve can make it easier to slide and/or rotate the anchoring device into position as it exits the delivery catheter with less-friction and being less likely to cause abrasions or damage to the native tissue than the surface of the anchoring device. The low-friction sleeve can be removable (e.g., by pulling proximally on the sleeve while holding a pusher and the anchoring device in place) after the anchoring device is in position in the native valve, e.g., to expose the surface of the anchoring device, which can be or include portions configured (porous, braided, large surface area, etc.) to promote tissue ingrowth.

The delivery catheter configurations described herein provide example embodiments that allow for accurate positioning and deployment of an anchoring device. However, in some instances, retrieval or partial retrieval of the anchoring device can still be necessary at any stage during or after deployment of the anchoring device in order, for example, to reposition the anchoring device at the native valve, or to remove the anchoring device from the implant site. The below embodiments describe various locks or lock-release mechanisms that can be used for attaching and/or detaching an anchoring or docking device from a deployment pusher that pushes the anchoring device out of the delivery catheter. Other locks or locking mechanisms are also possible, e.g., as described in U.S. Provisional Patent Application Ser. No. 62/560,962, filed on Sep. 20, 2017 incorporated by reference herein. The anchoring device can be connected at its proximal side to a pusher or other mechanism that can push, pull, and easily detach from the anchoring device. Further features of the systems, apparatuses, and methods disclosed herein that may be utilized are described in U.S. patent application Ser. No. 15/984,661 (U.S. Publication No. 2018/0318079), filed May 21, 2018, the entire contents of which are incorporated by reference herein.

In embodiments, the various manipulations and controls of the systems and devices described herein can be automated and/or motorized. For example, the controls or knobs described above can be buttons or electrical inputs that cause the actions described with respect to the controls/knobs above. This can be done by connecting (directly or indirectly) some or all of the moving parts to a motor (e.g., an electrical motor, pneumatic motor, hydraulic motor, etc.) that is actuated by the buttons or electrical inputs. For example, the motor can be configured, when actuated, to cause tethers such as control wires or pull wires to tension or relax to move the distal region of the catheter. Additionally or alternatively, the motor could configured, when actuated, to cause a device such as a pusher to move translationally or axially relative to the catheter to cause an anchoring or docking device to move within and/or into or out of the catheter. Automatic stops or preventative measures could be built in to prevent damage to the system/device and/or patient, e.g., to prevent movement of a component beyond a certain point.

It should be noted that the devices and apparatuses described herein can be used with other surgical procedures and access points (e.g., transapical, open heart, etc.). It should also be noted that the devices described herein (e.g., the deployment tools) can also be used in combination with various other types of anchoring devices and/or prosthetic valves different from the examples described herein.

For purposes of this description, certain aspects, advantages, and novel features of the embodiments of this disclosure are described herein. The disclosed methods, apparatuses, and systems should not be construed as limiting in any way. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved. Features, elements, or components of one embodiment can be combined into other embodiments herein.

Although the operations of some of the disclosed embodiments are described in a particular, sequential order for convenient presentation, it should be understood that this manner of description encompasses rearrangement, unless a particular ordering is required by specific language. For example, operations described sequentially can in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms can vary depending on the particular implementation and are readily discernible by one of ordinary skill in the art. Steps of various methods herein can be combined.

In view of the many possible embodiments to which the principles of the disclosure can be applied, it should be recognized that the illustrated embodiments are only preferred examples of the invention and should not be taken as limiting the scope of the disclosure. Rather, the scope of the disclosure is defined by the following claims.

What is claimed is:

1. A system for delivering an implant to a portion of a patient's body, the system comprising:
   a delivery catheter including:
      an elongate shaft having a flexible portion,
      a spine including an elongate strip extending longitudinally in a spiral along a first portion of the flexible portion,
      a tether extending longitudinally in a spiral along a second portion of the flexible portion that is circumferentially spaced from the first portion, and
      wherein the flexible portion is configured to form a spiral shape upon a longitudinal force being applied to the tether.

2. The system of claim 1, wherein the flexible portion includes an inner lumen for the implant to be passed through.

3. The system of claim 2, wherein the spine and the tether spiral about the inner lumen.

4. The system of claim 2, wherein the first portion is positioned opposite from the second portion across the inner lumen.

5. The system of claim 1, wherein the spiral of the elongate strip forms at least a half rotation about the flexible portion.

6. The system of claim 1, wherein the spiral of the elongate strip forms at least a three-quarters rotation about the flexible portion.

7. The system of claim 1, wherein the spiral of the elongate strip forms at least a full rotation about the flexible portion.

8. The system of claim 1, wherein a pitch of the spiral of the elongate strip varies along a length of the flexible portion.

9. The system of claim 1, wherein the elongate strip includes a cut-out portion extending longitudinally along the elongate strip.

10. The system of claim 1, wherein a proximal portion of the spine couples to a passively flexible portion of the elongate shaft.

11. The system of claim 1, further comprising material having a lower durometer than the spine positioned circumferentially adjacent to the spine.

12. The system of claim 1, wherein the spine and the tether are embedded in a body of the elongate shaft.

13. The system of claim 1, further comprising a tether channel extending longitudinally in a spiral along the second portion of the flexible portion and configured to receive the tether.

14. The system of claim 1, wherein the spiral shape of the flexible portion is helical.

15. The system of claim 1, wherein the tether comprises a pull tether configured to be retracted proximally to form the flexible portion into the spiral shape.

16. The system of claim 1, wherein the flexible portion is configured to move from a straightened shape to the spiral shape.

17. The system of claim 16, wherein the flexible portion is configured to move from the straightened shape to the spiral shape to vary a direction of a distal tip of the elongate shaft.

18. The system of claim 16, wherein the flexible portion is configured to move from the spiral shape to the straightened shape.

19. The system of claim 1, further comprising a steerable guide sheath including a lumen for the elongate shaft to pass through, the steerable guide sheath configured to deflect a portion of the elongate shaft when the elongate shaft is positioned within the lumen of the steerable guide sheath.

20. The system of claim 1, further comprising the implant, and wherein the implant comprises a docking coil.

\* \* \* \* \*